US005466671A

United States Patent [19]

Tempst et al.

[11] Patent Number: 5,466,671

[45] Date of Patent: Nov. 14, 1995

[54] APIDAECIN-TYPE PEPTIDE ANTIBIOTICS WITH IMPROVED ACTIVITIES AND/OR DIFFERENT ANTIBACTERIAL SPECTRUM

[75] Inventors: Paul Tempst, New York, N.Y.; Peter Casteels, Erpe-Mere, Belgium

[73] Assignee: Sloan-Kettering Institute for Cancer Research, New York, N.Y.

[21] Appl. No.: 205,938

[22] Filed: Mar. 2, 1994

[51] Int. Cl.[6] .......................... A01N 63/02; A61K 38/10; C07K 7/00; C07K 7/08

[52] U.S. Cl. ............................ 514/13; 514/14; 530/326; 530/327

[58] Field of Search ................................ 514/12, 13, 14; 530/300, 324, 325, 326, 327, 350

[56] References Cited

U.S. PATENT DOCUMENTS 5,300,629 4/1994 Casteels et al. ........................ 530/326

FOREIGN PATENT DOCUMENTS 0182278 5/1986 European Pat. Off. .
0299828 1/1989 European Pat. Off. .
8800976 2/1988 WIPO .

OTHER PUBLICATIONS

Keppi, et al., *C.R. Acad. Sc. Paris* (1986) 303(5): 155–160.

P. van Hofsten, et al., *Proc. Natl. Acad. Sci.—USA* (Apr. 1985) 82(8): 2240–2243.

Andreu, et al., *Proc. Natl. Acad. Sci.—USA* (Nov. 1983) 80(21):6475–6479.

Dimarcq, et al., *Euro. Jour. of Bioch.* (Jan. (II) 1988) 171(½): 17–22.

Casteels—Josson, et al., *The EMBO Journal* (1993) 12(4): 1569–1578.

Boman and Hultmark, *Annual Review of Microbiology* (1987) 41: 103–126.

Jaynes, et al., *BioEssays* (Jun. 1987) 6(6): 263–270.

Zasloff, Proc. Natl. Acad. Sci. U.S.A. 84:5449–5453 (1987).

*Primary Examiner*—Charles L. Patterson, Jr.
*Assistant Examiner*—Eric Grimes
*Attorney, Agent, or Firm*—John P. White

[57] ABSTRACT

This invention provides a purified polypeptide having antibacterial activity comprising a first sequence Pro-Arg-Pro-Pro-His-Pro-Arg-X1, wherein X1 is Ile or Leu; and a second sequence X2-Pro-X3-X4-X5-Pro, wherein X2 is Arg or Lys, X3 is Thr, Gln or Arg, X4 is Tyr, Gln or Pro, and X5 is Val or Ala, the second sequence is N-terminal to the first sequence. This invention also provides a purified polypeptide having antibacterial activity comprising: a first sequence, at least seven amino acid residues are the same as Pro-Arg-Pro-Pro-His-Pro-Arg-X1, wherein X1 is Ile or Leu; a second sequence X2-Pro-X3-X4X5-Pro, wherein X2 is Arg or Lys, X3 is Thr, Gln or Arg, X4 is Tyr, Gln or Pro, and X5 is Val or Ala, the second sequence is N-terminal to the first sequence; and a third sequence comprising at least five amino acid residues, at least one-third of the residues are Pro, the third sequence is N-terminal to the second sequence.

15 Claims, 2 Drawing Sheets

| | | 1 2 a b c 3 5 7 9 a b 10 13 15 18 | [MH+] calculated | [m/z] obtained |
|---|---|---|---|---|
| Honey bee | Hb Ia | G N - - N R P V Y I P - Q P R P P H P R I | 2109.46 | n.d. |
| | Hb Ib | . . . . . . . . . . . - . . . . . . . . L | 2109.46 | 2110.0 |
| | Hb II | . . . . . . . I . . . - . . . . . . . . . | 2123.48 | n.d. |
| | Hb III | . . . . . . . . . . S - . . . . . . . . . | 2099.42 | n.a. |
| Bumble bee | Bb +A | A - - - N R P V Y I P - P P R P P H P R L | 1978.36 | 1978.5 |
| | Bb -A | . . . . . . . - . . . . . . . . . | 1907.28 | 1907.8 |
| Cicada Killer | Ck P | N R P T Y V P - P P R P P H P R L | 1894.22 | 1894.0 |
| | Ck A | . . . . . . . - A . . . . . . . . | 1869.19 | 1868.2 |
| Bald-faced hornet | Ho + | G - K P - R P Q Q V P - - P R P P H P R L | 1958.33 | 1960.0 |
| | Ho - | . . . . . . - - . . . . . . . . | 1675.99 | n.a. |
| Yellow jacket & german wasp | Yj +S | S N K P - R P Q Q V P - - P R P P H P R L | 2102.46 | 2102.9 |
| | Yj -S | . . . - . . . . . . - - . . . . . . . . | 2015.38 | 2015.8 |
| *C. disparis* | Cd 1+ | G - K P N R P R P A P I Q P R P P H P R L | 2282.72 | 2281.4 |
| | Cd 1- | . . . . . . . . . . . . . . . . . | 2000.38 | 2001.1 |
| | Cd 2+ | . - . . . K . . . . . . K . . . . . . . . | 2254.75 | 2255.3 |
| | Cd 2- | . K . . . . . . K . . . . . . . . | 1972.40 | n.a |
| | Cd 3+ | . - . . S K . . . . . . K . . . . . . . . | 2227.72 | 2227.8 |
| | Cd 3- | S K . . . . . . K . . . . . . . . | 1945.38 | 1945.3 |

Conserved Sequence: R/K P ... P ... P R P P H P R I/L

FIGURE 1

Positions: 1 2 a b c 3 5 7 9 a b 10 13 15 18

| | | Sequence | [MH+] calculated | [m/z] obtained |
|---|---|---|---|---|
| Honey bee | Hb Ia | G N - - N R P V Y I P - Q P R P P H P R I | 2109.46 | n.d. |
| | Hb Ib | . . . . . . . . . . . - . . . . . . . . L | 2109.46 | 2110.0 |
| | Hb II | . . . . . . . I . . . - . . . . . . . . . | 2123.48 | n.d. |
| | Hb III | . . . . . . . . . . S - . . . . . . . . . | 2099.42 | n.a. |
| Bumble bee | Bb +A | A - - - N R P V Y I P - P P R P P H P R L | 1978.36 | 1978.5 |
| | Bb -A | . . . . . . . - . . . . . . . . . | 1907.28 | 1907.8 |
| Cicada Killer | Ck P | N R P T Y V P - P P R P P H P R L | 1894.22 | 1894.0 |
| | Ck A | . . . . . . . - A . . . . . . . . | 1869.19 | 1868.2 |
| Bald-faced hornet | Ho + | G - K P - R P Q Q V P - - P R P P H P R L | 1958.33 | 1960.0 |
| | Ho - | . . . . . . - - . . . . . . . . . | 1675.99 | n.a. |
| Yellow jacket & german wasp | Yj +S | S N K P - R P Q Q V P - - P R P P H P R L | 2102.46 | 2102.9 |
| | Yj -S | . . . - . . . . . . - - . . . . . . . . . | 2015.38 | 2015.8 |
| *C. disparis* | Cd 1+ | G - K P N R P R P A P I Q P R P P H P R L | 2282.72 | 2281.4 |
| | Cd 1- | . . . . . . . . . . . . . . . . . . . | 2000.38 | 2001.1 |
| | Cd 2+ | . - . . . K . . . . . . K . . . . . . . . | 2254.75 | 2255.3 |
| | Cd 2- | . K . . . . . . K . . . . . . . . | 1972.40 | n.a |
| | Cd 3+ | . - . . S K . . . . . . K . . . . . . . . | 2227.72 | 2227.8 |
| | Cd 3- | S K . . . . . . K . . . . . . . . | 1945.38 | 1945.3 |

Conserved Sequence: R/K P … P … P R P P H P R I/L

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 8
( D ) OTHER INFORMATION: /note="Residue 8 is Ile or Leu."

( x i ) SEQUENCE DESCRIPTION: SEQ ID NO:1:

```
Pro Arg Pro Pro His Pro Arg Xaa
1               5
```

( 2 ) INFORMATION FOR SEQ ID NO:2:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:

-continued ( A ) NAME/KEY: Peptide
( B ) LOCATION: 1..5
( D ) OTHER INFORMATION: /note="Residue 1 is Arg or Lys.
Residue 3 is Thr, Gln or Arg.
Residue 4 is Tyr, Gln or Pro.
Residue 5 is Val or Ala."

( x i ) SEQUENCE DESCRIPTION: SEQ ID NO:2:

Xaa Pro Xaa Xaa Xaa Pro
1 5

( 2 ) INFORMATION FOR SEQ ID NO:3:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Arg Pro Thr Tyr Val Pro
1 5

( 2 ) INFORMATION FOR SEQ ID NO:4:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:4:

Arg Pro Gln Gln Val Pro
1 5

( 2 ) INFORMATION FOR SEQ ID NO:5:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:5:

Arg Pro Arg Pro Ala Pro
1 5

( 2 ) INFORMATION FOR SEQ ID NO:6:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:6:

Lys Pro Arg Pro Ala Pro
1 5

( 2 ) INFORMATION FOR SEQ ID NO:7:

( i ) SEQUENCE CHARACTERISTICS:
( A ) LENGTH: 16 amino acids
( B ) TYPE: amino acid
( D ) TOPOLOGY: linear -continued ( i i ) MOLECULE TYPE: peptide ( x i ) SEQUENCE DESCRIPTION: SEQ ID NO:7:

Asn Arg Pro Thr Tyr Val Pro Pro Pro Arg Pro Pro His Pro Arg Leu
1 5 10 15

( 2 ) INFORMATION FOR SEQ ID NO:8:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( x i ) SEQUENCE DESCRIPTION: SEQ ID NO:8:

Asn Arg Pro Thr Tyr Val Pro Ala Pro Arg Pro Pro His Pro Arg Leu
1 5 10 15

( 2 ) INFORMATION FOR SEQ ID NO:9:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:9:

Gly Lys Pro Arg Pro Gln Gln Val Pro Pro Arg Pro Pro His Pro Arg Leu
1 5 10 15

( 2 ) INFORMATION FOR SEQ ID NO:10:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( x i ) SEQUENCE DESCRIPTION: SEQ ID NO:10:

Arg Pro Gln Gln Val Pro Pro Arg Pro Pro His Pro Arg Leu
1 5 10

( 2 ) INFORMATION FOR SEQ ID NO:11:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Ser Asn Lys Pro Arg Pro Gln Gln Val Pro Pro Arg Pro Pro His Pro Arg
1 5 10 15

( 2 ) INFORMATION FOR SEQ ID NO:12:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:12:

-continued

Asn Lys Pro Arg Pro Gln Gln Val Pro Pro Arg Pro Pro His Pro Arg Leu
1 5 10 15

( 2 ) INFORMATION FOR SEQ ID NO:13:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( x i ) SEQUENCE DESCRIPTION: SEQ ID NO:13:

Gly Lys Pro Asn Arg Pro Arg Pro Ala Pro Ile Gln Pro Arg Pro Pro
1 5 10 15

His Pro Arg Leu
20

( 2 ) INFORMATION FOR SEQ ID NO:14:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:14:

Asn Arg Pro Arg Pro Ala Pro Ile Gln Pro Arg Pro Pro His Pro Arg Leu
1 5 10 15

( 2 ) INFORMATION FOR SEQ ID NO:15:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( x i ) SEQUENCE DESCRIPTION: SEQ ID NO:15:

Gly Lys Pro Asn Lys Pro Arg Pro Ala Pro Ile Lys Pro Arg Pro Pro
1 5 10 15

His Pro Arg Leu
20

( 2 ) INFORMATION FOR SEQ ID NO:16:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:16:

Asn Lys Pro Arg Pro Ala Pro Ile Lys Pro Arg Pro Pro His Pro Arg Leu
1 5 10 15

( 2 ) INFORMATION FOR SEQ ID NO:17:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide -continued ( x i ) SEQUENCE DESCRIPTION: SEQ ID NO:17:

Gly Lys Pro Ser Lys Pro Arg Pro Ala Pro Ile Lys Pro Arg Pro Pro
1 5 10 15

His Pro Arg Leu
20

( 2 ) INFORMATION FOR SEQ ID NO:18:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:18:

Ser Lys Pro Arg Pro Ala Pro Ile Lys Pro Arg Pro Pro His Pro Arg Leu
1 5 10 15

( 2 ) INFORMATION FOR SEQ ID NO:19:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 3..8
( D ) OTHER INFORMATION: /note="Residue 8 is Ile or Leu."

( x i ) SEQUENCE DESCRIPTION: SEQ ID NO:19:

Pro Arg Xaa Pro His Pro Arg Xaa
1 5

( 2 ) INFORMATION FOR SEQ ID NO:20:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:20:

Ser Gln Pro Arg Pro Gln Pro
1 5

( 2 ) INFORMATION FOR SEQ ID NO:21:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( x i ) SEQUENCE DESCRIPTION: SEQ ID NO:21:

Gln Val Pro Ile Arg Pro Ser Gln Pro Arg Pro Gln Pro
1 5 10

( 2 ) INFORMATION FOR SEQ ID NO:22:

( i ) SEQUENCE CHARACTERISTICS:
( A ) LENGTH: 18 amino acids

-continued ( B ) TYPE: amino acid
( D ) TOPOLOGY: linear ( i i ) MOLECULE TYPE: peptide ( x i ) SEQUENCE DESCRIPTION: SEQ ID NO:22:

Ser Arg Pro Ser Pro Gln Val Pro Ile Arg Pro Ser Gln Pro Arg Pro Gln
1 5 10 15

( 2 ) INFORMATION FOR SEQ ID NO:23:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:23:

Gly Asn Asn Arg Pro Val Tyr Ile Pro Gln Pro Arg Pro Pro His Pro
1 5 10 15

Arg Ile ( 2 ) INFORMATION FOR SEQ ID NO:24:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:24:

Gly Asn Asn Arg Pro Val Tyr Ile Pro Gln Pro Arg Pro Pro His Pro
1 5 10 15

Arg Leu ( 2 ) INFORMATION FOR SEQ ID NO:25:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:25:

Gly Asn Asn Arg Pro Ile Tyr Ile Pro Gln Pro Arg Pro Pro His Pro
1 5 10 15

Arg Ile ( 2 ) INFORMATION FOR SEQ ID NO:26:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:26:

Gly Asn Asn Arg Pro Val Tyr Ile Ser Gln Pro Arg Pro Pro His Pro
1 5 10 15

-continued

Arg Ile ( 2 ) INFORMATION FOR SEQ ID NO:27:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:27:

Ala Asn Arg Pro Val Tyr Ile Pro Pro Pro Arg Pro Pro His Pro Arg
1 5 10 15

Leu ( 2 ) INFORMATION FOR SEQ ID NO:28:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

Asn Arg Pro Val Tyr Ile Pro Pro Pro Arg Pro Pro His Pro Arg Leu
1 5 10 15

( 2 ) INFORMATION FOR SEQ ID NO:29:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:29:

Gly Lys Pro Arg Pro Gln Gln Val Pro Pro Arg Pro Pro His Pro Arg
1 5 10 15

Leu ( 2 ) INFORMATION FOR SEQ ID NO:30:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:30:

Gly Lys Pro Arg Pro Tyr Ser Pro Arg Pro Thr Ser His Pro Arg Pro
1 5 10 15

Ile Arg Val ( 2 ) INFORMATION FOR SEQ ID NO:31:

( i ) SEQUENCE CHARACTERISTICS:
( A ) LENGTH: 8 amino acids
( B ) TYPE: amino acid -continued ( C ) STRANDEDNESS: single
( D ) TOPOLOGY: linear ( i i ) MOLECULE TYPE: peptide ( x i ) SEQUENCE DESCRIPTION: SEQ ID NO:31:

Pro Arg Pro Pro His Pro Arg Leu
1 5

( 2 ) INFORMATION FOR SEQ ID NO:32:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:32:

Gly Lys Pro Arg Pro Gln Gln Val Pro Pro Arg Pro Pro His Pro Arg
1 5 10 15

Leu ( 2 ) INFORMATION FOR SEQ ID NO:33:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

Ser Arg Pro Ser Pro Gln Val Pro Ile Arg Pro Ser Gln Pro Arg Pro
1 5 10 15

Gln Pro Gly Lys Pro Arg Pro Gln Gln Val Pro Pro Arg Pro Pro His
20 25 30

Pro Arg Leu
35

( 2 ) INFORMATION FOR SEQ ID NO:34:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:34:

Phe Lys Pro Arg Pro Gln Gln Val Pro Pro Arg Pro Pro His Pro Arg
1 5 10 15

Leu ( 2 ) INFORMATION FOR SEQ ID NO:35:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: peptide -continued ( x i ) SEQUENCE DESCRIPTION: SEQ ID NO:35:

Ser Arg Pro Ser Pro Gln Val Pro Ile Arg Pro Ser Gln Pro Arg Pro
1 5 10 15

Gln Pro Phe Lys Pro Arg Pro Gln Gln Val Pro Pro Arg Pro Pro His
20 25 30

Pro Arg Leu
35

( 2 ) INFORMATION FOR SEQ ID NO:36:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:36:

Gly Lys Pro Arg Pro Gln Gln Val Pro Pro Arg Thr Pro His Pro Arg
1 5 10 15

Leu ( 2 ) INFORMATION FOR SEQ ID NO:37:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:37:

Ser Arg Pro Ser Pro Gln Val Pro Ile Arg Pro Ser Gln Pro Arg Pro
1 5 10 15

Gln Pro Gly Lys Pro Arg Pro Gln Gln Val Pro Pro Arg Thr Pro His
20 25 30

Pro Arg Lys
35

( 2 ) INFORMATION FOR SEQ ID NO:38:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:38:

Phe Lys Pro Arg Pro Gln Gln Val Pro Pro Arg Thr Pro His Pro Arg
1 5 10 15

Leu ( 2 ) INFORMATION FOR SEQ ID NO:39:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: peptide -continued ( x i ) SEQUENCE DESCRIPTION: SEQ ID NO:39:

Ser Arg Pro Ser Pro Gln Val Pro Ile Arg Pro Ser Gln Pro Arg Pro
1 5 10 15

Gln Pro Phe Lys Pro Arg Pro Gln Gln Val Pro Pro Arg Thr Pro His
20 25 30

Pro Arg Leu
35

( 2 ) INFORMATION FOR SEQ ID NO:40:

( i ) SEQUENCE CHARACTERISTICS:
( A ) LENGTH: 30 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:40:

Gln Val Pro Ile Arg Pro Ser Gln Pro Arg Pro Gln Pro Phe Lys Pro
1 5 10 15

Arg Pro Gln Gln Val Pro Pro Arg Thr Pro His Pro Arg Leu
20 25 30

( 2 ) INFORMATION FOR SEQ ID NO:41:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:41:

Ser Gln Pro Arg Pro Gln Pro Phe Lys Pro Arg Pro Gln Gln Val Pro
1 5 10 15

Pro Arg Thr Pro His Pro Arg Leu
20

( 2 ) INFORMATION FOR SEQ ID NO:42:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:42:

Ser Asn Lys Pro
1

( 2 ) INFORMATION FOR SEQ ID NO:43:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 4
( D ) OTHER INFORMATION: /note="Residue 4 is Asn or Ser."

-continued ( x i ) SEQUENCE DESCRIPTION: SEQ ID NO:43:

Gly Lys Pro Xaa
1

APIDAECIN-TYPE PEPTIDE ANTIBIOTICS WITH IMPROVED ACTIVITIES AND/OR DIFFERENT ANTIBACTERIAL SPECTRUM

BACKGROUND OF THE INVENTION

Throughout this application, various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

The following standard abbreviations are used throughout to refer to amino acids:

| | | | | | |
|---|---|---|---|---|---|
| A | Ala | Alanine | M | Met | Methionine |
| C | Cys | Cysteine | N | Asn | Asparagine |
| D | Asp | Aspartic acid | P | Pro | Proline |
| E | Glu | Glutamic acid | Q | Gln | Glutamine |
| F | Phe | Phenylalanine | R | Arg | Arginine |
| G | Gly | Glycine | S | Ser | Serine |
| H | His | Histidine | T | Thr | Threonine |
| I | Ile | Isoleucine | V | Val | Valine |
| K | Lys | Lysine | W | Trp | Tryptophan |
| L | Leu | Leucine | Y | Tyr | Tyrosine |

Other abbreviations include the following. PBS: phosphate buffered saline, BSA: bovine serum albumin, MeCN: acetonitrile, TFA: trifluoro acetic acid, Fmoc: 9-fluoroenyl-methoxycarbonyl, PTH: phenyl thiohydantoin, RP-HPLC: reversed-phase high performance liquid chromatography, MALDI-TOF: matrix-assisted laser-desorption ionization time-of-flight, MS: mass spectrometry, UV: ultra violet, ELISA: enzyme-linked immunosorbent assay, RT: room temperature, MIC: minimal inhibitory concentration, CFU: colony forming units, nt: not tested.

For more than a century, it has been known that bacteria are among the agents of disease. Disinfectants and antibiotics usually allow to contain unwanted microbial propagation, but not always. The exceptions thus necessitate a continuing search for novel antibiotics. During the last decade, many antibacterial peptides have been isolated from insects (for latest updates see Refs. 1 and 2, and references therein). While undoubtedly vital for the insects, to date, no strong efforts have been made to assess the prospects of clinical applications. Published accounts on screening insect peptides for activity against severe human pathogens or genuinely problematic, opportunistic bacteria are unavailable.

It is well-established however, that the overwhelming majority of antibacterial peptides, including the well-studied defensins, cecropins and magainins, function through a 'lytic/ionophoric' mechanism (3–11). Common theme among all 'lyric' peptides is a permeabilizing effect on bacterial cytoplasmic membranes. A cationic, amphipathic structure that enables formation of hydrophilic ion (proton) channels in a lipid bilayer (12) is fundamental to this activity; proton leakage causes dissipation of the membrane potential, required for many vital life processes, thus causing cell death (7,8,13,14). As perturbation of membranes by these peptides is not dependent on recognition of chiral molecules (15,16), amino acid substitutions that do not abrogate general amphipathic structure or basic net charge are functionally tolerated (17,18).

Even if selected peptide antibiotics are of initial therapeutic efficacy, meaningful, long-term medical applications could only be considered after finding a way to target lethal activities to well-chosen groups of microbes, to cope with emerging resistance, and to create more stable, less antigenic and easier to produce analogs. In other words, will antibacterial peptides be amenable to specific manipulations (amino acid substitutions, deletions or truncations) leading to the synthesis of second generation chemotherapeutics, that are widely applicable and economically justified, or would offer a specific solution to recognized problems in antimicrobial therapy, such as treatment of infections in immuno-compromised hosts (19), resistant (20) or persistent strains (21), bacteremias (22) and previously unrecognized pathogens (23)? Rational modifications to existing peptides must be guided by the results of prior, detailed structure/function analyses. Obviously, short peptides offer distinct advantages for such studies. In addition, because of their generic lethal mechanism, 'lyric' peptides may not be particularly suited as backbone for those developments.

A unique peptide, 'apidaecin', has been isolated from honeybees (24). Apidaecin is small (18 unmodified, L-amino acids; 33% proline) and can easily be mass produced. The peptide inhibits viability of many gram negative bacteria in nanomolar doses; gram positives are unaffected. Lethal activity is near immediate and shown to be independent of the conventional 'lyric' mechanism (25). In addition, apidaecin-resistant mutants are of undiminished sensitivity to 'pore-forming' peptides and the D-enantiomer is devoid of antibacterial activities . The current model is that the antagonistic effects of apidaecin on bacteria involve stereoselective recognition of chiral targets (25).

Understanding of the role played by each component amino acid in apidaecin might be obtained from exhaustive functional screening of synthetic analogs. This approach could easily develop into an unmanageable project as, for instance, producing combinatorial change in 6 positions would equal screening 64 million peptides, without any guarantee of an improved product. Although 'de-novo' peptide (6–7 residues) drug design using such combinatorial approaches (also known as peptide libraries) have been suggested (26), trying to accomplish this in the context of a 20 residue long peptide would be infinitely more difficult and labor intensive. Instead, nature (i.e. evolution) was turned to in order to understand structure/function of bioactive peptides. Insects are an ideal source of peptide to initiate such comparative structural analysis for reasons of (i) enormous evolutionary diversity (27,28), (ii) ease of rearing, handling, and inducing and harvesting peptide antibiotics, and (iii) their strong reliance on those peptides for immunity and, consequently, survival.

SUMMARY OF THE INVENTION

This invention provides a purified polypeptide having antibacterial activity comprising a first sequence Pro-Arg-Pro-Pro-His-Pro-Arg-X1 (SEQ ID NO: 1), wherein X1 is Ile or Leu; and a second sequence X2-Pro-X3-X4-X5-Pro (SEQ ID NO: 2), wherein X2 is Arg or Lys, X3 is Thr, Gln or Arg, X4 is Tyr, Gln or Pro, and X5 is Val or Ala, the second sequence is N-terminal to the first sequence.

This invention provides a purified polypeptide having antibacterial activity comprising:

a first sequence, at least seven amino acid residues are the same as Pro-Arg-Pro-Pro-His-Pro-Arg-X1 (SEQ ID NO: 1), wherein X1 is Ile or Leu;

a second sequence X2-Pro-X3-X4-X5-Pro (SEQ ID NO: 2), wherein X2 is Arg or Lys, X3 is Thr, Gln or Arg, X4 is Tyr, Gln or Pro, and X5 is Val or Ala, the second sequence is N-terminal to the first sequence; and a third sequence comprising at least five amino acid residues, at least one-third of the residues are Pro, the third sequence is N-terminal to the second sequence.

This invention provides DNA encoding a polypeptide as described above.

This invention provides a purified antibody capable of binding to a polypeptide as described above.

This invention provides a method for determining the presence of the polypeptide in a sample comprising: incubating the sample with the antibody described above, and detecting an antibody-antigen complex, thereby determining the presence of the polypeptide in the sample.

This invention provides a method for inhibiting growth of a bacterium comprising administering to the bacterium a growth inhibiting effective concentration of a polypeptide as described above.

This invention provides a pharmaceutical composition comprising an antibacterial effective amount of a polypeptide as described above.

This invention provides a method for treating a subject infected with a bacterium comprising administering to the subject an antibacterial effective amount of a polypeptide as described above, thereby treating the subject.

This invention provides a method for obtaining a purified apidaecin-like polypeptide from a Hymenopteran insect comprising:

obtaining a sample of lymph from the insect;

treating the sample so as to obtain supernatant;

applying the supernatant to a reversed-phase high performance liquid chromatography column;

eluting from the column;

collecting the fractions eluted from the column; and determining a fraction which contains the polypeptide, thereby obtaining the polypeptide from the insect.

DESCRIPTION OF THE FIGURES

FIG. 1. Sequence alignment of apidaecin-type peptides. Numbering is based on the honeybee (Hb) sequences (24); naturally occurring isoforms are grouped per insect (separated by dotted lines). Dots (.) indicate that the residue in this position is identical to the one in the primary sequence (top line in each box) of that particular insect; dashes (—) represent a gap in the sequence, introduced for alignment purposes. Sequence similarities are boxed (solid lines) and the conserved consensus sequence is shown at the bottom (also boxed). [$MH^+$] is the theoretical molecular weight (average isotopic mass), calculated from the proposed sequence (using Procomp software); [m/z] values were experimentally obtained by MALDI-TOF mass spectrometric analysis. ND means not done; NA is not applicable (reason being that these peptides have never been observed in nature). Peptides Hb III was predicted from cDNA sequences (35); peptides Ho— and Cd2— were artificially lacking in GKP for comparative purposes.

DETAILED DESCRIPTION OF THE INVENTION

Figure 2:
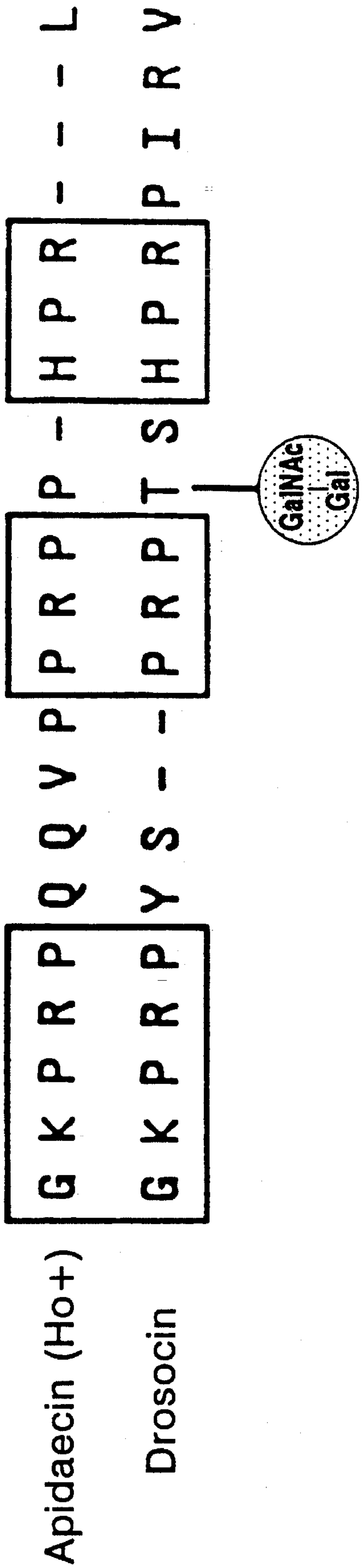
FIG. 2. Sequence alignment between hornet apidaecin and drosocin from *Drosophila*. Dashes (- ) represent gaps, introduced for optimal alignment; identical residues are boxed. The drosocin structure is taken from Ref. 2; GalNAc-Gal stands for N-acetylgalactosamine-galactose (O-linked to Thr).

This invention provides a purified polypeptide having antibacterial activity comprising a first sequence Pro-Arg-Pro-Pro-His-Pro-Arg-X1 (SEQ ID NO: 1), wherein X1 is Ile or Leu; and a second sequence X2-Pro-X3-X4-XS-Pro (SEQ ID NO: 2), wherein X2 is Arg or Lys, X3 is Thr, Gln or Arg, X4 is Tyr, Gln or Pro, and X5 is Val or Ala, the second sequence is N-terminal to the first sequence.

In an embodiment the polypeptide has up to about thirty-five amino acid residues. In another embodiment the polypeptide has from about fourteen to about twenty-one amino acid residues.

While there is no limitation on the number of amino acid residues separating the first and second sequences, in a specific embodiment the second sequence is separated from the first sequence by up to two amino acid residues.

In an embodiment of the polypeptide, the second sequence is selected from the group consisting of:

Arg-Pro-Thr-Tyr-Val-Pro (SEQ ID NO: 3),

Arg-Pro-Gln-Gln-Val-Pro (SEQ ID NO: 4),

Arg-Pro-Arg-Pro-Ala-Pro (SEQ ID NO: 5), and

Lys-Pro-Arg-Pro-Ala-Pro (SEQ ID NO: 6).

This invention also provides the polypeptide, further comprising a third sequence selected from the group consisting of Gly-Lys-Pro and Asn-Lys-Pro, and Phe-Lys-Pro; the third sequence is N-terminal to the second sequence. While there is no limitation on the number of amino acid residues separating the second and third sequences, in a specific embodiment the third sequence is separated from the second sequence by up to two amino acid residues. In a specific embodiment, the second sequence is selected from the group consisting of:

Arg-Pro-Gln-Gln-Val-Pro (SEQ ID NO: 4),

Arg-Pro-Arg-Pro-Ala-Pro (SEQ ID NO: 5), and

Lys-Pro-Arg-Pro-Ala-Pro (SEQ ID NO: 6).

In an embodiment, the polypeptide comprises a sequence selected from the group consisting of:

Asn—Arg—Pro—Thr—Tyr—Val—Pro—Pro—Pro—Arg—Pro—Pro—His—Pro—Arg—Leu (SEQ ID NO: 7);

Asn—Arg—Pro—Thr—Tyr—Val—Pro—Ala—Pro—Arg—Pro—Pro—His—Pro—Arg—Leu (SEQ ID NO: 8);

Gly—Lys—Pro—Arg—Pro—Gln—Gln—Val—Pro—Pro—Arg—Pro—Pro—His—Pro—Arg—Leu (SEQ ID NO: 9);

Arg—Pro—Gln—Gln—Val—Pro—Pro—Arg—Pro—Pro—His—Pro—Arg—Leu (SEQ ID NO: 10);

Ser—Asn—Lys—Pro—Arg—Pro—Gln—Gln—Val—Pro—Pro—Arg—Pro—Pro—His—Pro—Arg—Leu (SEQ ID NO: 11);

Asn—Lys—Pro—Arg—Pro—Gln—Gln—Val—Pro—Pro—Arg—Pro—Pro—His—

-continued

Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

In a more specific embodiment the polypeptide is selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Arg—Pro—Gln—Gln—Val—Pro—Pro—Arg—Pro—Pro—His—Pro—Arg—Leu (SEQ ID NO: 10);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

This invention further provides nucleic acid encoding the purified antibacterial polypeptide. Starting with an amino acid sequence, various nucleic acid molecules which encode the amino acid sequence can be generated based on the genetic code, which is known to those of skill in the art. The nucleic acid molecule can be either DNA or RNA, single stranded or double stranded. The single stranded molecule can be either the top (coding) or bottom (noncoding) strand. The single stranded nucleic acid molecule is useful as a probe. In a preferred embodiment this invention provides for a plasmid capable of expressing the polypeptide. The plasmid contains transcriptional and translational control sequences known to those of skill in the art.

This invention provides a purified polypeptide having antibacterial activity isolatable from an insect; the insect is selected from the group consisting of *Sphecius speciosus, Vespula maculata, Vespula maculifrons, Paravespula germanica*, and *Coccygomimus disparis*; the polypeptide comprising the sequence Pro-Arg-Pro-Pro-His-Pro-Arg. In an embodiment, the polypeptide is isolated from the lymph of the insect. In a preferred embodiment the polypeptide is isolated from an immuno-induced insect.

This invention also provides purified polypeptide having antibacterial activity isolatable from an insect; the insect is selected from the group consisting of *Sphecius speciosus, Vespula maculata, Vespula maculifrons, Paravespula germanica*, and *Coccygomimus disparis*; the polypeptide characterized by binding to an anti-apidaecin antibody. In an embodiment, the polypeptide is isolated from the lymph of the insect. In a preferred embodiment the polypeptide is isolated from an immuno-induced insect.

This invention provides a purified antibody capable of binding to the polypeptide described herein. In an embodiment the antibody is a rabbit antibody. In one embodiment the antibody is a polyclonal antibody. In another embodiment the antibody is a monoclonal antibody.

This invention further provides a method for obtaining the purified antibody capable of binding to the polypeptide described herein comprising:

coupling an antigen selected from the group consisting of honeybee apidaecin and the polypeptide to a carrier protein;

immunizing a mammal with the coupled antigen; and isolating the antibody from the mammal, thereby obtaining the purified antibody.

The coupling of an antigen which is poorly immunogenic to a carrier protein is known to those of skill in the art. Various carrier proteins are known to those of skill in the art. In an embodiment of the above method for obtaining the purified antibody capable of binding to the polypeptide described herein, the carrier protein is tuberculin purified protein derivative. In an embodiment the immunizing is immunizing by injecting. In a preferred embodiment the mammal is a rabbit.

This invention provides a method for determining the presence of the polypeptide in a sample comprising: incubating the sample with the antibody described above, and detecting an antibody-antigen complex, thereby determining the presence of the polypeptide in the sample.

In the above method, the step of detecting the antibody-antigen complex can be performed in a number of ways known to one of skill in the art. In a preferred embodiment, the detecting comprises detecting by enzyme-linked immunoassay. In another embodiment, the detecting comprises radioimmunoassay.

This invention provides a method for inhibiting growth of a bacterium comprising administering to the bacterium a growth inhibiting effective concentration of the polypeptide described herein.

In an embodiment, this invention provides a method for inhibiting growth of a bacterium selected from the group consisting of:

*Escherichia coli, Enterobacter cloacae*, and *Erwinia amylovora, Klebsiella pneumoniae, Salmonella typhimurium, Shigella dysenteriae*, and *Pseudomonas syringae;* comprising administering to the bacterium a growth inhibiting effective concentration of a polypeptide selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Arg—Pro—Gln—Gln—Val—Pro—Pro—Arg—Pro—Pro—His—Pro—Arg—Leu (SEQ ID NO: 10);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

This invention also provides a method for inhibiting growth of an apidaecin resistant strain of *Escherichia coli* comprising administering a growth inhibiting effective concentration of a polypeptide selected from the group consisting of:

Gly—Lys—Pro—Arg—Pro—Gln—Gln—Val—Pro—Pro—Arg—Pro—Pro—His—Pro—Arg—Leu (SEQ ID NO: 9);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);

-continued

| |
|---|
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and |
| Ser—Lys—Pro—Arg—Pro—Ala—Pro—Ile—Lys—Pro—Arg—Pro—Pro—His—Pro—Arg—Leu (SEQ ID NO: 18). |

This invention also provides a method for inhibiting growth of Morganella morganii comprising administering a growth inhibiting effective concentration of a polypeptide selected from the group consisting of:

| |
|---|
| Gly—Lys—Pro—Arg—Pro—Gln—Gln—Val—Pro—Pro—Arg—Pro—Pro—His—Pro—Arg—Leu (SEQ ID NO: 9); |
| Arg—Pro—Gln—Gln—Val—Pro—Pro—Arg—Pro—Pro—His—Pro—Arg—Leu (SEQ ID NO: 10); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and |
| Ser—Lys—Pro—Arg—Pro—Ala—Pro—Ile—Lys—Pro—Arg—Pro—Pro—His—Pro—Arg—Leu (SEQ ID NO: 18). |

This invention also provides a method for inhibiting growth of Salmonella typhi comprising administering a growth inhibiting effective concentration of a polypeptide selected from the group consisting of:

| |
|---|
| Asn—Arg—Pro—Thr—Tyr—Val—Pro—Pro—Pro—Arg—Pro—Pro—His—Pro—Arg—Leu (SEQ ID NO: 7); |
| Asn—Arg—Pro—Thr—Tyr—Val—Pro—Ala—Pro—Arg—Pro—Pro—His—Pro—Arg—Leu (SEQ ID NO: 8); |
| Gly—Lys—Pro—Arg—Pro—Gln—Gln—Val—Pro—Pro—Arg—Pro—Pro—His—Pro—Arg—Leu (SEQ ID NO: 9); |
| Arg—Pro—Gln—Gln—Val—Pro—Pro—Arg—Pro—Pro—His—Pro—Arg—Leu (SEQ ID NO: 10); |
| Ser—Asn—Lys—Pro—Arg—Pro—Gln—Gln—Val—Pro—Pro—Arg—Pro—Pro—His—Pro—Arg—Leu (SEQ ID NO: 11); |
| Asn—Lys—Pro—Arg—Pro—Gln—Gln—Val—Pro—Pro—Arg—Pro—Pro—His—Pro—Arg—Leu (SEQ ID NO: 12); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); and |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17). |

This invention also provides a method for inhibiting growth of *Yersinia enterocolitica* comprising administering a growth inhibiting effective concentration of a polypeptide selected from the group consisting of:

| |
|---|
| Asn—Arg—Pro—Thr—Tyr—Val—Pro—Pro—Pro—Arg—Pro—Pro—His—Pro—Arg—Leu (SEQ ID NO: 7); |
| Asn—Arg—Pro—Thr—Tyr—Val—Pro—Ala—Pro—Arg—Pro—Pro—His—Pro—Arg—Leu (SEQ ID NO: 8); |
| Gly—Lys—Pro—Arg—Pro—Gln—Gln—Val—Pro—Pro—Arg—Pro—Pro—His—Pro—Arg—Leu (SEQ ID NO: 9); |

-continued

| |
|---|
| Arg—Pro—Gln—Gln—Val—Pro—Pro—Arg—Pro—Pro—His—Pro—Arg—Leu (SEQ ID NO: 10); |
| Asn—Lys—Pro—Arg—Pro—Gln—Gln—Val—Pro—Pro—Arg—Pro—Pro—His—Pro—Arg—Leu (SEQ ID NO: 12); and |
| Asn—Arg—Pro—Arg—Pro—Ala—Pro—Ile—Gln—Pro—Arg—Pro—Pro—His—Pro—Arg—Leu (SEQ ID NO: 14). |

This invention also provides a method for inhibiting growth of *Campylobacter jejuni* comprising administering a growth inhibiting effective concentration of a polypeptide selected from the group consisting of:

| |
|---|
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and |
| Ser—Lys—Pro—Arg—Pro—Ala—Pro—Ile—Lys—Pro—Arg—Pro—Pro—His—Pro—Arg—Leu (SEQ ID NO: 18). |

This invention provides a method for inhibiting growth of *Acinetobacter calcoaceticus* comprising administering a growth inhibiting effective concentration of a polypeptide selected from the group consisting of:

| |
|---|
| Gly—Lys—Pro—Arg—Pro—Gln—Gln—Val—Pro—Pro—Arg—Pro—Pro—His—Pro—Arg—Leu (SEQ ID NO: 9); |
| Ser—Asn—Lys—Pro—Arg—Pro—Gln—Gln—Val—Pro—Pro—Arg—Pro—Pro—His—Pro—Arg—Leu (SEQ ID NO: 11); |
| Asn—Lys—Pro—Arg—Pro—Gln—Gln—Val—Pro—Pro—Arg—Pro—Pro—His—Pro—Arg—Leu (SEQ ID NO: 12); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and |
| Ser—Lys—Pro—Arg—Pro—Ala—Pro—Ile—Lys—Pro—Arg—Pro—Pro—His—Pro—Arg—Leu (SEQ ID NO: 18). |

This invention also provides a method for inhibiting growth of Agrobacterium tumefaciens comprising administering a growth inhibiting effective concentration of a polypeptide selected from the group consisting of:

| |
|---|
| Asn—Arg—Pro—Thr—Tyr—Val—Pro—Pro—Pro—Arg—Pro—Pro—His—Pro—Arg—Leu (SEQ ID NO: 7); |
| Asn—Arg—Pro—Thr—Tyr—Val—Pro—Ala—Pro—Arg—Pro—Pro—His—Pro—Arg—Leu (SEQ ID NO: 8); |
| Gly—Lys—Pro—Arg—Pro—Gln—Gln—Val—Pro—Pro—Arg—Pro—Pro—His—Pro—Arg—Leu (SEQ ID NO: 9); |
| Asn—Lys—Pro—Arg—Pro—Gln—Gln—Val—Pro—Pro—Arg—Pro—Pro—His—Pro—Arg—Leu (SEQ ID NO: 12); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |

-continued

Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

This invention also provides a method for inhibiting growth of *Francisella tularensis* or *Haemophilus influenzae* comprising administering a growth inhibiting effective concentration of a polypeptide selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

This invention also provides a method for inhibiting growth of Legionella pneumophila comprising administering a growth inhibiting effective concentration of a polypeptide selected from the group consisting of:

Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

This invention also provides a method for inhibiting growth of *Rhizobium meliloti* comprising administering a growth inhibiting effective concentration of a polypeptide selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Arg—Pro—Gln—Gln—Val—Pro—Pro—Arg—Pro—Pro—His—Pro—Arg—Leu (SEQ ID NO: 10);

-continued

Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

This invention provides a pharmaceutical composition comprising an antibacterial effective amount of the polypeptide described herein and a pharmaceutically acceptable carrier. Pharmaceutically acceptable carriers are known to those with skill in the art. Examples include buffered saline solution and starch. In specific embodiments the pharmaceutical composition is a liquid, a cream, or a solid such as a tablet.

This invention provides a method for treating a subject infected with a bacterium comprising administering to the subject an antibacterial effective amount of a polypeptide described above, thereby treating the subject. In an embodiment, the subject is a mammalian subject. In a more specific embodiment the subject is a human subject. The polypeptide is administered according to techniques known to those of skill in the art, including orally, parenterally, intraperitoneally, by intramuscular injection, by intravenous injection, or topically.

This invention provides a method for obtaining a purified apidaecin-like polypeptide from a Hymenopteran insect comprising:

obtaining a sample of lymph from the insect;

treating the sample so as to obtain supernatant;

applying the supernatant to a reversed-phase high performance liquid chromatography column;
eluting from the column;

collecting the fractions eluted from the column; and determining a fraction which contains the polypeptide, thereby obtaining the polypeptide from the insect.

In a preferred embodiment of the method for obtaining a purified apidaecin-like polypeptide from a Hymenopteran insect, the obtaining a sample of lymph comprises puncturing the abdomen of the insect and collecting the hemolymph. In an embodiment the treating comprises centrifuging. In a preferred embodiment wherein the eluting is eluting with an ascending acetonitrile gradient. In an embodiment the determining is determining by enzyme-linked immunoassay, preferably comprising a first antibody being an anti-honey-bee-apidaecin antibody. In a preferred embodiment the first antibody is a polyclonal antibody.

A preferred embodiment further comprises, before obtaining a sample of insect lymph, immuno-inducing the insect. In an embodiment the immuno-inducing comprises infecting the insect with an immune-response-inducing effective amount of bacterium, such as *E. coli.*

This invention provides a purified polypeptide having antibacterial activity comprising:

a first sequence, at least seven amino acid residues are the same as Pro-Arg-Pro-Pro-His-Pro-Arg-X1 (SEQ ID NO: 1), wherein X1 is Ile or Leu;

a second sequence X2-Pro-X3-X4-X5-Pro (SEQ ID NO: 2), wherein
X2 is Arg or Lys,
X3 is Thr, Gln or Arg,
X4 is Tyr, Gln or Pro, and
X5 is Val or Ala, the second sequence is N-terminal to the first sequence; and a third sequence comprising at least five amino acid residues, at least one-third of the residues are Pro, the third sequence is N-terminal to the second sequence.

In an embodiment the polypeptide has up to about thirty-five amino acid residues.

While there is no limitation on the number of amino acid residues separating the sequences, in an embodiment the second sequence is separated from the first sequence by up to two amino acid residues. In another embodiment the second sequence is separated from the third sequence by up to three amino acid residues.

In an embodiment of the above polypeptide the first sequence is Pro-Arg-X6-Pro-His-Pro-Arg-X1 (SEQ ID NO: 19), wherein X6 is an amino acid residue. In an embodiment X6 is Pro. In another embodiment X6 is Thr.

In an embodiment, the third sequence comprises at least 13 amino acid residues. In a specific embodiment, at least one of every three consecutive amino acid residues is Pro. In an embodiment the third sequence comprises Pro-Arg-Pro.

In a specific embodiment the third sequence is selected from the group consisting of:
Ser-Gln-Pro-Arg-Pro-Gln-Pro (SEQ ID NO: 20),
Gln-Val-pro-Ile-Arg-Pro-Ser-Gln-Pro-Arg-Pro-Gln-Pro (SEQ ID NO: 21), and
Ser-Arg-pro-Ser-Pro-Gln-Val-Pro-Ile-Arg-Pro-Ser-Gln-Pro-Arg-Pro-Gln-Pro (SEQ ID NO: 22).

This invention further provides nucleic acid encoding the purified antibacterial polypeptide. The nucleic acid molecule can be either DNA or RNA, single stranded or double stranded. The single stranded molecule can be either the top (coding) or bottom (noncoding) strand. The single stranded nucleic acid molecule is useful as a probe. In a preferred embodiment this invention provides for a plasmid capable of expressing the polypeptide. The plasmid contains transcriptional and translational control sequences known to those of skill in the art.

This invention provides a purified antibody capable of binding to the polypeptide described herein. In an embodiment the antibody is a rabbit antibody. In one embodiment the antibody is a polyclonal antibody. In another embodiment the antibody is a monoclonal antibody.

This invention further provides a method for obtaining the purified antibody capable of binding to the polypeptide described herein comprising:

coupling an antigen selected from the group consisting of honeybee apidaecin and the polypeptide to a carrier protein;

immunizing a mammal with the coupled antigen; and isolating the antibody from the mammal, thereby obtaining the purified antibody.

The coupling of an antigen which is poorly immunogenic to a carrier protein is known to those of skill in the art. Various carrier proteins are known to those of skill in the art. In an embodiment of the above method for obtaining the purified antibody capable of binding to the polypeptide described herein, the carrier protein is tuberculin purified protein derivative. In an embodiment the immunizing is immunizing by injecting. In a preferred embodiment the mammal is a rabbit.

This invention provides a method for determining the presence of the polypeptide in a sample comprising: incubating the sample with the antibody described above, and detecting an antibody-antigen complex, thereby determining the presence of the polypeptide in the sample.

In the above method, the step of detecting the antibody-antigen complex can be performed in a number of ways known to one of skill in the art. In a preferred embodiment, the detecting comprises detecting by enzyme-linked immunoassay. In another embodiment, the detecting comprises radioimmunoassay.

This invention provides a method for inhibiting growth of a bacterium comprising administering to the bacterium a growth inhibiting effective concentration of the polypeptide described herein.

This invention provides a method for determining the presence of the polypeptide in a sample comprising: incubating the sample with the antibody described above, and detecting an antibody-antigen complex, thereby determining the presence of the polypeptide in the sample.

In the above method, the step of detecting the antibody-antigen complex can be performed in a number of ways known to one of skill in the art. In a preferred embodiment, the detecting comprises detecting by enzyme-linked immunoassay. In another embodiment, the detecting comprises radioimmunoassay.

This invention provides a method for inhibiting growth of a bacterium comprising administering to the bacterium a growth inhibiting effective concentration of the polypeptide described herein.

This invention provides a pharmaceutical composition comprising an antibacterial effective amount of the polypeptide described herein and a pharmaceutically acceptable carrier. Pharmaceutically acceptable carriers are known to those with skill in the art. Examples include buffered saline solution and starch. In specific embodiments the pharmaceutical composition is a liquid, a cream, or a solid such as a tablet.

This invention provides a method for treating a subject infected with a bacterium comprising administering to the subject an antibacterial effective amount of a polypeptide described above, thereby treating the subject. In an embodiment, the subject is a mammalian subject. In a more specific embodiment the subject is a human subject. The polypeptide is administered according to techniques known to those of skill in the art, including orally, parenterally, intraperitoneally, by intramuscular injection, by intravenous injection, or topically.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Introduction

Isolation and structural characterization of 13 novel, naturally occurring apidaecin-type peptides, and functional analysis (antibacterial spectra against medically relevant strains) of 17 members of this class of antibiotics are reported. Evolutionary 'conserved' and 'variable' regions in the apidaecin structure are delineated. Whereas it is speculated that conserved structures are responsible for general antibacterial capacity, it is clearly demonstrated that the natural diversity of the variable regions confers specificity to the antibacterial spectrum of each analog. Ability of certain homologs to overcome bacterial resistance against related peptides also resides in variable region biodiversity.

EXPERIMENTAL PROCEDURES

Immuno-Induction of Insects

Hymenopteran insects used for immuno-induction are listed in table 1 and were obtained from (collected at) the following sources (locations): *N. autumnalis* from Dr. Michael R. Wagner (Forest Pest Management, Northern Arizona University, Flagstaff, Ariz.), *C. desantisi* and *G. legneri* from Dr. Richard Tassan (Division of Biological Control, U. of California, Berkeley, Calif.), *C. disparis* and *B. intermedia* from Dr. Paul W. Schaefer (Beneficial Insects Introduction Research, USDA-ARS North Atlantic Region, Newark, Del.), *S. speciosus* from Central Park (NYC, N.Y.), *V. maculifrons* from underground nest (West Milford, N.J.), *V. maculata* from tree nest (Middletown, N.J.), *P. germanica* from underground nest (Erpe Mere, Belgium), *C. pennsylvanicus* from Carolina Biological Supply Company (Burlington, N.C.), *A. mellifera* from Mr. Robert Cornetto (West Milford, N.J.), *B. terrestris* from Prof. Frans Jacobs (Insect Research Center, Ghent State University, Belgium). Insects (1 to 10, depending on availability) were injected with $1–5\times10^4$ (depending on insect size) viable *E. coli* cells (ATCC 11775) suspended in 1 μl phosphate-buffered saline (PBS[1]: 0.15M, pH 7.2) A glass capillary (narrowed in the flame) was used for this purpose and alternatively, for the smallest insects such as the parasitic wasps, infections were carried out by clipping one wing with micro scissors or puncturing a leg with the tip of a hypodermic needle dipped for at least 30 seconds in a suspension of the same *E. coli* cells ($10^6$/μl). Insects were always sedated using $CO_2$ during manipulations. One day after infection, the insects were bled by puncturing the abdomen with a glass capillary. The collected hemolymph (0.5–2 μl) was pooled in ice-cooled tubes containing 100 μl of 2%TFA to prevent proteolytic degradation of the immuno-induced peptides and to precipitate proteins. Owing to their small size, total extracts were prepared from *C .desantisi* and *G. legneri* by homogenizing them in 2%TFA. The precipitate was spun down and the clear supernatant was frozen at −80° C.

TABLE I

Insects screened for presence of apidaecin-type peptides:
CLASS: Hexapoda (insecta)
ORDER: Hymenoptera

| SUBORDER | SUPER-FAMILY | FAMILY | SPECIES |
|---|---|---|---|
| Symphyta | Tenthredi-noida | Diprionidae | *Neodiprion autumnalis* |

TABLE I-continued

Insects screened for presence of apidaecin-type peptides:
CLASS: Hexapoda (insecta)
ORDER: Hymenoptera

| SUBORDER | SUPER-FAMILY | FAMILY | SPECIES |
|---|---|---|---|
| | | | (conifer sawflies) |
| Apocrita | Ichneumo-noidea | Ichneumonidae | *Coccygomimus disparis* (parasitic wasps) |
| | Chalcidoidea | Encyrtidae | *Copedosoma desantisi* (chalcids) |
| | | Chalcididae | *Brachymeria intermedia* (chalcids) |
| | Bethyloidea | Bethylidae | *Goniozus legneri* (parasitic wasps) |
| | Formicidae | (family not in superfamily) | *Camponotos pennsylvanicus* (carpenter ants) |
| | Vespoidea | Vespidae | *Vespula maculifrons* (yellow jackets) |
| | | | *Vespula maculata* (baldfaced hornets) |
| | | | *Paravespula germania* (german wasps) |
| | Sphecoidea | Sphecidae | *Sphecius speciosus* (cicada killers) |
| | Apoidea | Apidea | *Apis mellifera* (honeybees) |
| | | | *Bombus terrestris* (bumble bees) |

Classification from Borror, De Long and Triplehorn (1981) An Introduction to the Study of Insects, 5th edition, (W. B. Saunders, Philadelphis).

Reversed-Phase High Performance Liquid Chromatography

Depending on availability of "immune" lymph the primary fractionation by RP-HPLC was done on a 4.6 or 2.1×250 mm Vydac C4 (214TP54 or 214TP52) column from the Separation Group (Hesperia, CA) or on a 1×100 mm Inertsil 100GL-1-ODS-I10/5 C18 column from SGE (Ringwood, Australia). Standard bore (4.6 mm) columns were operated as described (1) using an AB 150A system (Applied Biosystems, Foster City, Calif.). Solvent A was 0.1% TFA (pH 2) and solvent B: 70% acetonitrile (MeCN) in A. Fractions were eluted at 1 ml/min, with a three-step linear gradient: 0–50%B/50 min, 50–70%B/10 min, 70–100%B/8 min (68 min total time), UV detection was done at 214 nm. A modular LC system was used for chromatography on 2.1 mm columns. Basic components of the system were an AB 140B syringe pump and an AB 1000S diode array detector. Full details about system assembly, plumbing, operational parameters and solvents have been described (29). Microbore columns (1 mm) were operated in a similar instrument, except that an AB model 783 variable wavelength detector, fitted with a LC-packings (San Francisco, Calif.) Kratos-compatible capillary flow cell which was directly connected to the column outlet was used; gradient slope was 1% B/min at a flow of 30 µl/min. Fractions were collected using a Pharmacia (Piscataway, N.J.) Frac 100 automated instrument (for the 4.6 mm column) or by hand (for the 2.1 and 1 mm columns) and put on ice; aliquots were removed at this point for ELISA, MS-analysis and analytical LC (on a smaller column). Repurifications were done on a variety of columns (different manufacturer, carbon chain length and carbon load, than the one for the primary run): Vydac C18, Vydac diphenyl, Aquapore RP300 (C8). Aside from the real-time stripchart recordings, chromatograms were also obtained on a PE Nelson (Cupertino, Calif.) data system using the 2700 Turbochrom (version 3) software.

Anti-Apidaecin Polyclonal Antisera

For adequate immunization of rabbits with apidaecin, the peptide had to be coupled to a tuberculin purified protein derivative (PPD) using a Cambridge Research Biochemicals (Cambridge, UK) immunization kit. Conjugation was done via the N-terminal amino group using glutaraldehyde and following the manufacturers protocol, except for some small modifications. Briefly, to the reaction vial, containing 75 µl PPD solution (10 mg/ml in 0.1M sodium hydrogen carbonate buffer pH 8.4), apidaecin (200µg dissolved in 75 µl of the same buffer) was added together with 5 µl glutaraldehyde (10% in buffer). The mixture was agitated and kept on room temperature for 18 h, five fold diluted with PBS and then dialyzed against PBS. The dialyzed solution (1 ml) was used for immunization of a rabbit, pre-vaccinated (with live Bacillus Calmette-Guerin) three weeks before injection, following the manufacturers schedule. In this way, anti-apidaecin antiserum was obtained for use in further studies. By itself, apidaecin is a very poor antigen.

Enzyme-Linked Immuno Assays (ELISA)

Aliquots from RP-HPLC column fractions (20/500 µl for 4.6 mm columns; 4/75 µl for 2.1 mm columns and 2/25 µl for 1 mm columns) or samples in MilliQ water (Millipore) were tested for the presence of apidaecin-like molecules by alkaline phosphatase based ELISA using anti-apidaecin (bee Hb Ia) polyclonal antiserum as the primary antibody. Tests were carried out essentially as described (30). Briefly, aliquots (see above) were mixed with 80 µl coat buffer (PBS pH=7.4 containing 6% saccharose and 1% PEG6000) in the wells of a 96-well micro titer plate (Costar EIA/RIA, Cambridge, Mass.) and incubated overnight at 4° C. The coat solution was discarded and the plates were blocked with 200 µl of a BSA solution (0.1%) in PBS for 1 h/RT, followed by two washes with PBS. Rabbit anti-apidaecin (bee) polyclonal antiserum (diluted 1/1000 in PBS/BSA) was then added and incubated for 1 hr/RT; plates were then washed five times with 0.1% Tween 80 in PBS. Subsequently, alkaline phosphatase conjugated goat anti-rabbit IgG (Sigma; diluted 1/1000 in PBS, containing 10 mg/ml BSA) was added, plates were incubated for 1 h/RT and then washed 5 times with the Tween/PBS solution. Enzyme substrate (1 mg/µl p-nitrophenyl phosphate in 10% diethanolamine, containing 0.5 mM $MgCl_2$ and 0.02% $NaN_3$, pH 9.2) was then added for 30 min/RT add the reaction terminated by addition of 50 µl 0.1M EDTA. Positives were scored by monitoring yellow color development though visual inspection and/or by measuring (at 405 nm) in a Titertek Multiscan microplate reader. A dilution series of synthetic bee apidaecin (1, 0.1, 0.01, 0.001 µg/ml) was used as a control.

Mass Spectrometry (MS)

HPLC column fractions, pure peaks and synthetic peptides were subjected to matrix-assisted laser desorption time-of-flight (MALDI-TOF) mass spectrometry (MS) analysis using a Vestec (Houston, Tex.) LaserTec instrument with a 337 run output nitrogen laser and a 1.2 m linear flight tube, as described (31). In general, 0.5 µl sample (in 20% MeCN containing 0.1% TFA) was mixed with 1 µl matrix (sinapinic acid or alpha-cyano-4-hydroxy cinnamic acid (ACCA)) solution, applied to the stainless steel probe tip and air dried before analysis. A 25 kV ion acceleration and 3 kV multiplier voltage were used. Typically, up to eight analyses were necessary for each data point, with varying matrices, sample concentrations and laser power. Laser power was varied between experiments as judged from optimal deflections of specific maxima, using a Tektronix (Beaverton, Oreg.) TDA 520 digitizing scope. Small amounts (1 picomole, 100 and 10 femtomoles) of synthetic bee apidaecin Hb Ib (average isotopic mass $MH^+$=2109.43) were added as an external control and to optimally calibrate the instrument. The nitrogen laser emits pulses of 400 microjoule at 337 run and is therefore a class IIIb laser product. All safety precautions were taken as set forth in booklet ANS Z136.1 of the Laser Institute of America.

Peptide Sequencing

Purified apidaecin-like peptides were sequenced with the aid of an Applied Biosystems model 477A automated sequenator, operated according to the principles outlined by Hewick et al (32). Stepwise liberated PTH-amino acids were identified using an "on-line" 120A HPLC system equipped with a PTH C18 (2.1×220 mm; 5 micron particle size) column (AB). The standard AB method was optimized for sub-picomole PTH analysis as described (33,34). It is well known that proline residues are cleaved rather slowly with concomitant developing lag in the sequencing cycles. Because apidaecins are very Pro-rich, a special sequencing cycle with double TFA-cleavage time (from 350 sec to 700 sec) was used. Extremely valuable information for interpretation of sequencing experiments came from the preceding mass-analyses; this helped in deconvoluting the signals for certain cycles (31). In the end, of course, the theoretical mass of the peptide (from sequencing results) must match experimental mass (from MS).

Chemical Peptide Synthesis

Chemical synthesis of apidaecin-type peptides and pig cecropin P1 was performed with an automated peptide synthesizer, model 430A (Applied Biosystems). 9-Fluoroenylmethoxycarbonyl (Fmoc)-N-protected, L-configuration amino acids were coupled sequentially to 4-hydroxymethylphenoxyacetic acid (HMP). Side chain protecting groups were: Asn, Gln and His (trityl), Arg (4- methoxy- 2,3,6-trimethylbenzenesulfonyl) and Tyr (t-butyl). The loading of the starting resin was 0.25 mmole (0.284 g HMP). The standard Applied Biosystems (AB) synthesis protocol 'FastMoc' was used, except that the first amino acid was triply coupled and the remaining free sites were blocked using acetic anhydride. All reagents and solvents were from AB. After completion of synthesis and removal of N-Fmoc group, 500 mg of the neutralized dried resin was cleaved for 4 hours in a 10 ml PolyPrep chromatography column (Biorad) with 10 ml of 82.5% TFA/ 5% phenol/ 5% thioanisole/ 5% water (V/V). After elution of the solution in a 50 ml conical vial, peptides were pelleted by precipitation in 25 ml ice cold tert-methyl butyl ether (3 times) and centrifugation, followed by solubilization in 20% acetic acid at a concentration of 25 mg/ml. The next step was to preparatively purify all peptides on a 2×25 cm Vydac C4 column, using the earlier described acetonitrile/TFA based solvent system, operated at a flow of 12 ml/min and a gradient slope of 1%B/min. The HPLC system was comprised of two model HPX pumps (Rainin Instruments, Woburn, Mass.) and an AB model 1000S diode array detector equipped with a preparative flow cell. Quality control of purified material was done by analytical HPLC and mass spectrometry before use in antibacterial tests.

Quantitation of Peptides

Stock solutions of all apidaecin-type peptides and cecropin P1, in highly purified water (MilliQ system, Millipore) or dilute acid (0.1–1% TFA), were quantitated by amino acid analysis. An automated amino acid analyzer with vapor-phase hydrolysis, AB model 420, was used for this purpose. Stocks were stored at −70° C. and periodically requantitated before dilution and use in activity tests. A quick way to assess approximate levels of apidaecin in solutions (pure or crude) is by analytical HPLC, as a measure of peak surface ($6\times10^5$ μV.sec corresponds to 1 μg peptide). The calibration curve hereby used was obtained from analyzing a dilution series of synthetic products. The calibration is linear in the 0.05 to 50 μg/ml range with a maximal error margin of 10% (35).

Bacterial Strains

All bacterial strains (except three) used in this study were obtained from the American Type Culture Collection (ATCC, Rockville, Md.); reasons for selection are discussed in the text. Grouping, according to Bergey's Manual of Determinative Bacteriology, ninth edition (Williams & Wilkins, Baltimore, Md.) , and strain numbers are as follows: Group 2: *Campylobacter jejuni* ATCC 33560, *Helicobacter pylori* ATCC 43504; Group 4A: *Acinetobacter calcoaceticus* ATCC 49137, *Agrobacterium tumefaciens* ATCC 15955, *Borderella pertussis* ATCC 9340, *Flavobacterium meningosepticum* ATCC 13253, *Francisella tularensis* ATCC 6223, *Legionella pneumophila* ATCC 33152, *Neisseria gonorrhoeae* ATCC 19424, *N. meningiditis* ATCC 13077, *Pseudomonas aeruginosa* ATCC 10145, *P. syringae* NCPPB 1106, *Rhizobium meliloti* ATCC 10310, *Xanthomonas maltophilia* ATCC 12714; Group 4B: *Bacteriodes melaninogenicus* ATCC 25845; Group 5.1 ('Enterobacteriaceae'): *Citrobacter freundii* ATCC 8090, *Escherichia coli* ATCC 25922 (clinical isolate) and 11775, *E. coli* 11775 Apid$^R$ (apidaecin- resistant strain derived from strain ATCC11775, see text), *E. coil* K514 (common strain from molecular cloning laboratory), *Enterobacter cloacae* ATCC 529, *Erwinia amylovora* ATCC 15580, *Klebsiella pneumoniae* ATCC 13883, *Morganella morganii* ATCC 25830, *Proteus mirabilis* ATCC 25933, *Salmonella typhimurium* ATCC 14028, *S. typhi* ATCC 6539, *Shigella dysenteriae* ATCC 13313, *Yersinia enterocolitica* ATCC 9610; Group 5.3: *Haemophilus ducreyi* ATCC 33940, *H. influenzae ATCC* 19418; Group 5.4: *Gardnerella vaginalis* ATCC 14018. All strains were handled under conditions and in a laboratory environment in compliance with Biosafety Level 2 for Infections Agents as set forth in HHS Publication No. (NIM) 88-8395 ("Biosafety in microbiological and biomedical laboratories"). At the conclusion of all experiments, the area was decontaminated and microorganisms destroyed by autoclaving.

Inhibition Zone Assay

Aliquots of all synthetic, purified, apidaecin-type peptide stocks were diluted (to 2.5 nmol/μl final concentration) in MilliQ water. Aliquots of 20 μl and controls (20 μl MQ water) were then applied in 3 mm diameter wells on agar plates seeded with log phase bacteria. Plates were incubated at 28° C. (plant associated bacteria and *E. cloacae, H. ducreyi, A. calcoaceticus & Y. enterocolitica*) or 37° C. (others) and inspected for inhibition zone development after 24 or 48 h; inhibition zones were then measured. In general, bacteria were grown on BHI (brain heart infusion) medium (Difco 0003) , except for Agrobacterium, Erwinia, *Pseudomonas syringae*, Acinetobacter and Morganella which were grown on nutrient agar, Campylobacter, Francisella, Gardnerella, Bacteriodes, Borderella and *Haemophilus ducreyi* on chocolate agar (Remel 01-300 plates), Legionella on cye agar (Remel 01-342 plates), *Haemophilus*

*influenzae* and Helicobacter on GC medium (Difco 0289) with 2% hemoglobin powder (BBL 11871) and Rhizobium on tryptic soy agar. All tests were done under aerobic conditions, except for Campylobacter and Helicobacter which were grown under micro-aerophilic conditions ('campypak') and Neisseria, Legionella and *Haemophilus ducreyi* under 5–10% $CO_2$ ('$CO_2$-pak').

Minimal Inhibitory Concentrations

Minimal inhibitory concentrations (MIC's) of all apidaecin-type peptides against selected bacterial strains were determined in flat-bottomed 96-well microtiter plates (Microtest III Tissue culture plate, Falcon); 10 μl aliquots of serial dilutions of peptides were added to 70 μl deionized water (MQ) and the mixture was in oculated with 20 μl of a bacterial suspension containing $3\times10^5$ (or less) viable cells in the appropriate growth medium (typically the same as for agar plate tests but minus the agar). Final peptide concentrations were 0, 0.01, 0.02, 0.05, 0.1, 0.2, 0.5, 1, 5, 10 and 20 μg/ml. The MIC values (a–b) express the highest peptide concentration at which cells were able to grow (a) and the lowest concentration at which no growth was observed (b), both after incubation at 28°–37° C. for at least 48 h.

RESULTS

Purification of Novel Apidaecin-Type Peptides

Structural constraints on antibacterial capacity of apidaecin through sequence comparison of homologous peptides, isolated from different insects were investigated. Previous, extensive studies have failed to detect the presence of apidaecin-type peptides in any insects outside the Hymenoptera order. Thus, twelve hymenopteran insects (listed in table 1) were chosen for analysis. They have been selected to represent both suborders (Symphyta and Apocrita) and seven out of the thirteen superfamilies (including all families not placed in superfamilies) that make up the largest (Apocrita) suborder (according to the classification in Ref. 27). Some of the species belong to the same superfamilies, or the same families even: honeybees and bumblebees (Apidae family); hornets, yellow jackets and german wasps (Vespidae family); one representative of the Encyrtidae family, one representative of the Chalcididae family (both members of the Chalcidoidea superfamily). It was felt that this should enable a determination of close and distant molecular evolutionary relationships, casting more light on the degree of conservation (and functional significance) of particular residues or stretches of sequence in the apidaecin molecule. Because the Symphyta suborder is very distinct from all other hymenopteran insects, there was a reasonable risk that they did not contain apidaecin-like peptides. Therefore, only one member of this suborder was chosen for study.

Immuno-induction was carried out on all selected insects table 1) and 'immune' lymph was harvested or total extracts were prepared. Acid stable molecules in 'crude' hemolymph or total extracts were fractionated by HPLC, and column fractions were screened for apidaecin homologs using enzyme-linked immuno assay (ELISA) with anti-apidaecin (bee Ib) antiserum. Positive peptide peaks were first checked by MALDI-TOF MS for the presence of molecules with $M_r$ in the 1,500 to 2,500 dalton range and then further purified to apparent homogeneity. To make sure that any 'apidaecin-like' peptides that did not cross-react with the antiserum and/or fell outside the expected molecular size brackets would not be overlooked, antibacterial testing against *E. coli* ATCC 11775 and *Bacillus megaterium* QMB1551 and Arthrobacter sp. NRRLB 3724 were carried out. Several additional antibacterial 'factors' were thus isolated (e.g. from chalcids and carpenter ants) and subsequently shown, by limited structural analysis, to be devoid of PP or PRP sequences (data not shown) that are characteristic for the Pro-Arg-rich family of peptide antibiotics. Due to insufficient source material, antibacterial testing was omitted on fractions derived from *C. desantisi* and *G. legneri.*

Following intense scrutiny, it appeared that not all hymenopteran insects secreted detectable levels of apidaecin-type peptides into their hemolymph in response to *E. coli* infections. They did however, produce other 'response-factors', some of which had outspoken antibacterial activities (2). In contrast, the cicada-killer wasp (*Sphecious speciosus*) produced a massive quantity of apidaecin (two different isoforms) but no significant levels of any other peptides.

Covalent Structures

From the earliest isolation and sequencing experiments, the presence of three apidaecin isoforms in honeybees (24) was known; the structures are shown in FIG. 1. While isoform Ib is clearly predominant in 'immune' lymph (90%), antibacterial spectra and specific activities are the same for all three peptides (24). More recent analysis of apidaecin cDNA clones indicated that the various peptides are generated by processing of single polyprotein precursors (35). Analysis of all putative isoforms, observed in the open reading frames, indicated the presence of a fourth species, apidaecin III (with Pro replaced by Ser at position 9; see FIG. 1), that had never been found in lymph.

Covalent structures of all newly isolated apidaecin-type peptides were studied by a combination of chemical microsequencing and mass spectrometry. Sequences are listed, in aligned format, in FIG. 1. Also shown in that table are theoretical (average isotopic mass) molecular weight values [$MH^+$], calculated from the proposed sequences using Procomp version 1.2 software (kindly provided by Dr. P. C. Andrews, Michigan U., Ann Arbor, Mich.), and the experimentally obtained m/z values. Only in a single case is the difference between theoretical and experimental mass >1.0 dalton (>0.05% error), namely for hornet peptide Ho+, where a discrepancy of 1.67 dalton was observed; this is still within limits of experimental error. Thus, chances that any of these peptides carry post-translational modifying moieties are virtually non-existing.

As is evident from the results shown in FIG. 1, microheterogeneities, in the form of ragged ends (likely due to incomplete processing or unfavorable exoproteolysis) and various isoforms, occur within certain insect species (honeybees, bumble bee, cicada killer, Coccygomimus). They were not easily separated by RP-HPLC, due in part to peak-broadening caused by racemization of proline bonds. Edman-sequencing data were further confounded by the abundance of proline residues, causing additional lag.

The accurate mass measurements allowed deconvolution of the mixed chemical sequencing results. A detailed account of these Edman-chemical/MALDI-TOF MS approaches to micro peptide sequencing has been given elsewhere (31).

From the proposed alignment in FIG. 1, it could be concluded that certain parts of the apidaecin-type peptides are indeed evolutionary conserved, notably a carboxy-terminally located stretch of eight amino acids (PRPPHPRL) (SER ID NO: 31), a R/K-P dipeptide (residues 4–5 in the Hb Ib sequence numbering) and a proline at position 9 (except in Hb III). Intervening and amino-terminal regions seem to be 'variable'. Not unexpectedly, these variations are rather subtle (single or double amino acid substitutions) between peptides from closely related insects (e.g. honeybees / bumble bees; wasps / hornets / yellow jackets) and more pronounced between, for instance, bees and distantly related parasitic wasps from the Ichneumonoidae superfamily. The only surprise was that, while peptides from two members of the genus Vespula (yellow jackets and hornets) were slightly different (by one residue), one of them (from yellow jackets) was identical to the major apidaecin-form isolated from a different genus (Paravespula; german wasp); this is mildly puzzling in that it seemingly violates the generally accepted correlation between taxonomic classification and molecular evolution (36).

Antibacterial Spectra

To examine possible effects of the observed sequence differences on antibacterial capacity and spectrum, testing against thirty two selected bacterial strains was initiated (see 'Experimental Procedures') using agar plate growth inhibition zone assays. These bacteria have been specifically chosen to bring together a relevant selection of non-virulent strains. Relevant, because they are representatives of bacterial species typically used as test-strains for evaluation of novel antibiotics (e.g. *E. coli, Klebsiella pneumoniae, Enterobacter cloacae, Citrobacter freundii, Proteus mirabilis, Morganella morganii, Acinetobacter calcoaceticus, Yersinia enterocolitica, Haemophilus influenzae*, Salmonella, *Neisseria gonorrhoeae, N. meningiditis, Xanthomonas maltophilia* and *Pseudomonas aeruginosa*) (37,38), and of such selected disease-causing microbes as *Borderella pertussis* (whooping cough), *Francisella tularensis* (tularemia) , *Legionella pneumophila* (form of pneumonia), *Gardnerella vaginalis* (ulcers), *Campylobacter jejuni* (enteric pathogen; estimated 2 million infections per year in the U.S.) and *Helicobacter pylori* (gastric ulcers) (39,40). As the *Salmonella typhimurium* strain, strain ATCC14028 was selected because it has been used extensively for genetic studies of virulence, including resistance against defensins (41). Four plant-associated bacteria were also included (as positive controls so to speak, since honeybee-derived antimicrobials are very active against them). *E. coli* strain 11775Apid$^R$ is a mutant derived from strain ATCC 11775 and is resistant to approximately 500-fold higher apidaecin (type Hb Ib) concentrations than the parental strain (MIC value against $10^7$ cells/ml of 50 μg/ml compared to 0.1 μg/ml) (25) . Interestingly, mutant and parental strain are equally susceptible to abaecin, a different Pro-rich 'immune' peptide from honeybees (42).

Due to limited availability, these studies started with rather small numbers of insects (e.g. 20 hornets, 4 cicada-killer wasps, 4 small parasitic wasps). As a result, only low picomolar quantities of purified peptides were available, largely insufficient to carry out antibacterial testing on the proposed scale. All known, naturally occuring apidaecin-type peptides (listed in FIG. 1) were therefore chemically synthesized, purified (50 mg each), quality controlled (by MS), and stock solutions made and quantitated (by amino acid composition analysis). Peptides Hb Ia and II were not included in further studies as they have been shown previously to be functionally similar to Hb Ib (24,43). Peptides Ho— and Cd2— have never been observed in nature but were included here to study the possible functional significance of the N-terminal GKP sequence. Cecropin P1 (synthetic product based on the published sequence (44) of a peptide isolated from pig intestine) was included as a representative of mammalian peptide antibiotics. Selection of this antibacterial peptide as a 'control' was based on the assumption that, because of the tissue and specific anatomical site from which it was isolated, activities against enteric bacteria and against certain pathogens that enter the body through the gastrointestinal tract were to be expected.

Results from antibacterial testing (in triplicate) of sixteen apidaecin-type peptides and cecropin P1 against the thirty two aforementioned bacterial strains are summarized in table 2. A number of observations can be readily made. 1) Artificial peptide Hb III, based on a gene sequence, and the only peptide carrying a substitution of conserved Pro(9), is essentially inactive against nearly all strains tested. 2) Several apidaecin-type peptides are clearly active against mutant *E. coli* strain 1175Apid$^R$, whereas others (including the 'original' honeybee peptide Ib) are most definitely not. 3) Additional functional variability, in terms of antibacterial spectra and specific activities, exists among apidaecin-type peptides, to the extent that apidaecin-analog-based antibiograms against certain bacteria are nearly 'mirror image' of one another (e.g. *Yersinia enterocolitica* compared to *Campylobacter jejuni*). 4) As a group, Coccygomimus-derived apidaecin-type peptides are somewhat less active against Enterobacteriaceae than all the other ones, but have moderately to significantly better activities against *Campylobacter jejuni, Legionella pneumophila* and *Haemophilus influenzae*. 5) All apidaecin-type peptides are completely inactive against several of the test strains; cecropin P1 has measurable activity against some of those resistant strains (e.g. *Haemophilus ducreyi, Xanthomonas maltophilia* and *Bacteriodes melaninogenicus*) but not against all (e.g. Neisseria strains, Proteus, Gardnerella and *Helicobacter pylori*). 6) Finally, and not unexpectedly, Apidaecin-type peptides have extraordinary activities against plant-associated bacteria (Erwinia, *Agrobacterium tumefaciens, Rhizobium meliloti* and *Pseudomonas syringae*); even defective peptide Hb III showed considerable activity whereas the otherwise very potent cecropin P1 did not (see Rhizobium and *P. syringae*, for instance).

Careful scrutiny of the apidaecin-type sequences (FIG. 1) and of the antibiograms in table 2 indicates that contrasting antibacterial spectra/specificities can be correlated, in several cases, with very subtle sequence differences. Table 3 contains illustrative examples of these fascinating structure/function correlations. Peptides Cd3—, 2—,1— differ by just one (S to N), or only two (K/K to R/Q) or three (S/K/K to N/R/Q) amino acids; the rest of the sequences are identical (see FIG. 1, table 3A). Thus, R/Q (at positions 4/10) confers strong antibacterial activity to apidaecins against *S. typhimurium* and *Yersinia enterocolitica* but incapacitates the same peptides as antibacterial agents against *Campylobacter jejuni* and *Legionella pneumophila*; K/K (at 4/10) totally reverses this specificity profile (table 4A). Peptide Hb Ib cosegregates with Cd—1 from Cd2—/3— by virtue of its specificity against the eight test strains listed in table 4. Interestingly, while substantially divergent in sequence from all three Cd-peptides, Hb Ib contains the same characteristic N/R/Q (3/4/10) motif as Cd2—, leaning further support to the notion that R/Q (4/10) is a specificity determining motif. As for the difference between Cd2— and Cd3—, the S to N (at position 3) substitution increases the specific activity against Erwinia amylovora. Peptides Ho+ and Yj–S also differ by just one residue (G to N) (see FIG. 1; table 3B). While the 'G'-form has substantially higher specific activities against *Francisella tularensis* and *Morganella morganii* than the 'N'-form, a full reversal of this specificity against *Acinetobacter calcoaceticus* and *Erwinia amylovora* is seen; no functional differences between the two peptides were observed against several *E. coli* strains. Ho/Yj– is identical to the former two peptides but lacks the first three amino acids (FIG. 1 and 3B). This G/N—K—P truncation eliminates antibacterial activities against many, but not all, bacteria; activities against the Morganella strain and *E. coli* ATCC11775 were unaffected. What this actually means, is that the presence or absence of these three amino acids at the amino-terminus of some apidaecin-type peptides critically determines capacity to overcome antibacterial resistance of *E. coli* mutant strain '11775apid$^R$'. A similar effect of a GKP truncation was observed for peptide Cd2+ (termed Cd2– after truncation), with a decrease of antibacterial activity against Campylobacter, Haemophilus and both Salmonella strains but with no measurable effect on activities against all other sensitive bacteria tested (table 2).

Key to Table II. Antibacterial Spectra of Sixteen Apidaecin-Type Peptides

Listed are the results of agar plate inhibition zone assays. Bacterial strain identification and growth conditions are given in 'Experimental Procedures'. Peptides (listed in top row; see FIG. 1 for abbreviation legends) were applied in 3 mm wells, 50 nanomoles/well for all apidaecins and 5 nanomoles/well for cecropin P1 (CP1). Number of plus signs express the diameter of the inhibition zones and can be read using the following key: (+) 5–6 mm; (++) 7–9 mm; (+++) 10–14 mm; (++++) 15–19 mm; (+++++) 20 or more min. (–) denotes that no inhibition was observed. Growth of *Helicobacter pylori, Flavobacterium meningosepticum, Neisseria gonorrhoeae, N. meningiditis, Gardnerella vaginalis, Proteus mirabilis, Borderella pertussis, Xanthomonas maltophilia, Haemophilus ducreyi, Bacteriodes melaninogenicus* and *Pseudomonas aeruginosa* was not inhibited by any of the apidaecin-type peptides.

Key to Table III. Effects of Subtle Amino Acid Substitutions on Antibacterial Specificity of Apidaecin-Type Peptides Listed is a small selection of the agar plate inhibition zone results from table 2; see table 2 for experimental conditions and scoring system. Specific amino acids present in a particular position in the peptide sequences (for numbering, see FIG. 1) are also listed. Peptides Cd3—, 2—, and 1— are identical except for the amino acid differences shown; HbIb differs by additional residues. Peptides Ho+ and Yj—S are also identical except for a G to N change in position 2*a*; (/) indicates the absence of amino acids.

Key to Table IV. Antibacterial Actvities of Apidaecin-Type Peptides

The minimal inhibitory concentration (MIC) of sixteen apidaecin-type peptides and cecropin P1 to inhibit growth of some representative strains are expressed in μg/ml. For details see 'Experimental Procedures'. Inoculum (in CFU/ml) is listed for each bacterial strain; *E. coli* strains ATCC11775 and 11775apid$^R$ were tested with two different inoculum sizes.

TABLE II

Panel A
Antibacterial spectra of sixteen apidaecin-type peptides.

| Bacteria | Hb Ib | Hb III | Bb–A | Bb+A |
|---|---|---|---|---|
| Enterobacteriaceae | | | | |
| *Escherichia coli* (ATCC11775) | ++++ | — | ++++ | ++++ |
| *Escherichia coli* (11775 Apid R) | — | — | — | — |
| *Escherichia coli* (K514) | +++ | — | +++ | +++ |
| *Enterobacter cloacae* | +++ | — | +++ | +++ |
| *Erwinia amylovora* | ++++ | — | ++++ | ++++ |
| *Klebsiella pneumoniae* | +++ | + | ++ | ++ |
| *Morganella morganii* | + | — | — | — |
| *Salmonella typhimurium* | +++ | + | +++ | +++ |
| *Salmonella typhi* | +++ | + | +++ | +++ |
| *Shigella dysenteriae* | ++++ | + | +++ | ++++ |
| *Yersinia enterocolitica* | +++ | ++ | +++ | +++ |
| Other Bacteria | | | | |
| *Campylobacter jejuni* | — | — | — | — |
| *Acinetobacter calcoaceticus* | + | — | ++ | ++ |
| *Agrobacterium tumefaciens* | +++++ | ++++ | ++++ | ++++ |
| *Francisella tularensis* | +++ | + | +++ | +++ |
| *Legionella pneumophila* | — | — | + | ++ |
| *Pseudomonas syringae* | ++++ | ++ | ++++ | +++++ |
| *Rhizobium* | +++++ | +++++ | +++++ | ++++ |

TABLE II-continued

| | | | | |
|---|---|---|---|---|
| *meliloti* | | | | |
| *Haemophilus influenzae* | +++ | nt | ++ | +++ |

Panel B
Antibacterial spectra of sixteen apidaecin-type peptides.

| Bacteria | Ck P | Ck A | Ho − | Ho + |
|---|---|---|---|---|
| Enterobacteriaceae | | | | |
| *Escherichia coli* (ATCC11775) | +++ | +++ | +++ | +++ |
| *Escherichia coli* (11775 Apid R) | — | — | — | +++ |
| *Escherichia coli* (K514) | ++ | ++ | — | +++ |
| *Enterobacter cloacae* | +++ | ++ | + | +++ |
| *Erwinia amylovora* | +++ | +++ | ++ | +++ |
| *Klebsiella pneumoniae* | ++ | ++ | + | +++ |
| *Morganella morganii* | — | — | ++ | ++ |
| *Salmonella typhimurium* | ++++ | +++ | + | +++ |
| *Salmonella typhi* | +++ | +++ | + | +++ |
| *Shigella dysenteriae* | ++++ | +++ | + | +++ |
| *Yersinia enterocolitica* | +++ | +++ | ++ | ++++ |
| Other Bacteria | | | | |
| *Campylobacter jejuni* | — | — | — | — |
| *Acinetobacter calcoaceticus* | — | — | — | + |
| *Agrobacterium tumefaciens* | ++++ | ++++ | — | ++ |
| *Francisella tularensis* | ++ | + | — | +++ |
| *Legionella pneumophila* | — | — | — | — |
| *Pseudomonas syringae* | ++++ | +++ | +++ | +++ |
| *Rhizobium meliloti* | +++++ | ++++ | ++++ | ++++ |
| *Haemophilus influenzae* | ++ | ++ | — | +++ |

Panel C
Antibacterial spectra of sixteen apidaecin-type peptides.

| Bacteria | Yj +S | Yj −S | Cd 1+ | Cd 1− |
|---|---|---|---|---|
| Enterobacteriaceae | | | | |
| *Escherichia coli* (ATCC11775) | +++ | +++ | ++ | +++ |
| *Escherichia coli* (11775 Apid R) | +++ | +++ | ++ | ++ |
| *Escherichia coli* (K514) | ++ | +++ | ++ | +++ |
| *Enterobacter cloacae* | ++ | ++ | +++ | +++ |
| *Erwinia amylovora* | +++ | ++++ | ++ | ++++ |
| *Klebsiella pneumoniae* | ++ | ++ | ++ | ++ |
| *Morganella morganii* | — | — | ++ | ++ |
| *Salmonella typhimurium* | +++ | +++ | ++ | +++ |
| *Salmonella typhi* | ++ | +++ | +++ | ++ |
| *Shigella dysenteriae* | ++++ | +++ | ++++ | +++ |

TABLE II-continued

| | | | | |
|---|---|---|---|---|
| *Yersinia enterocolitica* | — | ++ | — | ++ |
| Other Bacteria | | | | |
| *Campylobacter jejuni* | — | — | +++ | — |
| *Acinetobacter calcoaceticus* | + | ++ | ++ | ++ |
| *Agrobacterium tumefaciens* | — | ++ | ++++ | +++ |
| *Francisella tularensis* | ++ | + | +++ | ++ |
| *Legionella pneumophila* | — | — | ++ | — |
| *Pseudomonas syringae* | ++++ | ++++ | ++++ | ++++ |
| *Rhizobium meliloti* | nt | ++++ | ++++ | ++++ |
| *Haemophilus influenzae* | +++ | ++ | ++++ | +++ |

Panel D
Antibacterial spectra of sixteen apidaecin-type peptides.

| Bacteria | Cd 2+ | Cd 2− | Cd 3+ | Cd 3− | CP-1 500p |
|---|---|---|---|---|---|
| Enterobacteriaceae | | | | | |
| *Escherichia coli* (ATCC11775) | +++ | +++ | ++ | ++ | — |
| *Escherichia coli* (11775 Apid R) | +++ | ++ | ++ | ++ | — |
| *Escherichia coli* (K514) | ++ | ++ | + | + | + |
| *Enterobacter cloacae* | +++ | +++ | +++ | +++ | ++++ |
| *Erwinia amylovora* | ++ | +++ | + | + | nt |
| *Klebsiella pneumoniae* | ++ | ++ | ++ | ++ | + |
| *Morganella morganii* | ++ | ++ | ++ | ++ | — |
| *Salmonella typhimurium* | +++ | + | ++ | ++ | ++ |
| *Salmonella typhi* | +++ | + | ++ | — | +++++ |
| *Shigella dysenteriae* | +++ | ++ | +++ | ++ | ++++ |
| *Yersinia enterocolitica* | — | — | — | — | +++++ |
| Other Bacteria | | | | | |
| *Campylobacter jejuni* | +++++ | +++ | +++++ | ++++ | +++ |
| *Acinetobacter calcoaceticus* | + | + | + | + | ++ |
| *Agrobacterium tumefaciens* | +++ | ++++ | +++ | ++ | ++++ |
| *Francisella tularensis* | +++ | +++ | ++++ | +++ | — |
| *Legionella pneumophila* | +++ | ++ | ++ | ++ | +++++ |
| *Pseudomonas syringae* | +++ | +++ | ++ | ++ | — |
| *Rhizobium meliloti* | ++++ | +++ | +++ | ++++ | + |
| *Haemophilus influenzae* | ++++ | ++ | ++++ | +++ | ++++ |

TABLE III

Panel A1
Effects of subtle amino acid differences on antibacterial specificity of apidaecin-type peptides

| | Amino acid @ position | | | Bacteria *E. coli* | *Erwinia* | *Pseudomanas* | *Salmonella* |
|---|---|---|---|---|---|---|---|
| Peptide | 3 | 4 | 5 | K514 | *amylovora* | *syringae* | *typhimurium* |
| Cd 3– | S | K | K | + | + | ++ | ++ |
| Cd 2– | N | K | K | ++ | +++ | +++ | + |
| Cd 1– | N | R | Q | +++ | ++++ | ++++ | +++ |
| Hb Ib | N | R | Q | +++ | ++++ | ++++ | +++ |

Panel B1

| | 2a | 2b | 2c | *E. coli* 11775 | *E. coli* ApidR | *Agrobacterium tumefaciens* | *Haemophilus influenzae* |
|---|---|---|---|---|---|---|---|
| Ho + | G | K | P | +++ | +++ | ++ | +++ |
| Yj–S | N | K | P | +++ | +++ | ++ | ++ |
| Ho – | / | / | / | +++ | — | — | — |

Panel A2
Effects of subtle amino acid differences on antibacterial specificity of apidaecin-type peptides

| | Amino acid @ position | | | Bacteria *Salmonella* | *Yersinia* | *Campylobacter* | *Legionella* |
|---|---|---|---|---|---|---|---|
| Peptide | 3 | 4 | 5 | *typhi* | *enterocolitica* | *jejuni* | *pneumophila* |
| Cd 3– | S | K | K | — | — | ++++ | ++ |
| Cd 2– | N | K | K | + | — | +++ | ++ |
| Cd 1– | N | R | Q | ++ | ++ | — | — |
| Hb Ib | N | R | Q | +++ | +++ | — | — |

Panel B2

| | 2a | 2b | 2c | *Francisella tularensis* | *Morganella morganii* | *Acinetobacter calcoaceticus* | *Erwinia amylovora* |
|---|---|---|---|---|---|---|---|
| Ho + | G | K | P | +++ | ++ | + | +++ |
| Yj–S | N | K | P | + | — | ++ | ++++ |
| Ho– | / | / | / | — | ++ | — | ++ |

TABLE IV

Panel A
Antibacterial activities of apidaecin-type peptides

| Peptide | *E. coli* 11775 (1200 CFU/ml) | *E. coli* Apid$^R$ (1000 CFU/ml) | *E. coli* 23802 (5000 CFU/ml) | *E. coli* 25922 (1100 CFU/ml) | *E. coli* 11775 ($16 \times 10^6$ CFU/ml) |
|---|---|---|---|---|---|
| Hb Ib | <0.05 | 20–40 | 10–20 | 0.5–1 | 1–5 |
| Hb III | 0.1–0.5 | >40 | >40 | 20–40 | 20–40 |
| Bb – A | 0.1–0.5 | >40 | 10–20 | 1–5 | 1–5 |
| Bb + A | 0.05–0.1 | >40 | 10–20 | 0.5–1 | 0.5–1 |
| Ck P | 0.1–0.5 | >40 | 20–40 | 0.5–1 | 1–5 |
| Ck A | 0.1–0.5 | >40 | >40 | 1–5 | 1–5 |
| Ho– | 0.5–1 | >40 | >40 | 10–20 | 10–20 |
| Ho+ | 0.1–0.5 | 1–5 | 0.5–1 | 0.1–0.5 | 0.1–0.5 |
| Yj+S | 0.1–0.5 | 1–5 | 0.5–1 | 0.1–0.5 | 0.1–0.5 |
| Yj–S | 0.1–0.5 | 5–10 | 1–5 | 0.1–0.5 | 0.1–0.5 |
| Cd 1+ | 10–20 | 10–20 | 10–20 | 10–20 | >20 |
| Cd 1– | 0.5–1 | >40 | 5–10 | 0.5–1 | 0.5–1 |
| Cd 2+ | 0.1–0.5 | 0.5–1 | 0.1–0.5 | 0.1–0.5 | 0.1–0.5 |
| Cd 2– | 0.5–1 | 5–10 | 10–20 | 0.5–1 | 0.5–1 |
| Cd 3+ | 0.1–0.5 | 0.5–1 | 0.1–0.5 | 0.1–0.5 | 0.1–0.5 |
| Cd 3– | 0.1–0.5 | 5–10 | 5–10 | 0.5–1 | 0.5–1 |
| CP–1 | 0.2–1 | 0.2–1 | 0.2–1 | 0.2–1 | 0.2–1 |

TABLE IV-continued

The minimal inhibitory concentration (MIC) of sixteen apidaecin-type peptides and cecropin P1 to inhibit growth of some representative strains are expressed in μg/ml. For details see 'Experimental Procedures.' Inoculum (in CFU/ml) is listed for each bacterial strain; *E. coli* strains ATCC11775 and 11775Apid$^R$ were tested with two different inoculum sizes.

Panel B
Antibacterial activities of apidaecin-type peptides

| Peptide | *E. coli* Apid$^R$ ($12 \times 10^6$ CFU/ml) | *S. typhimurium* ($8 \times 10^6$ CFU/ml) | *A. calcoaceticus* ($16 \times 10^6$ CFU/ml) | *M. morganii* (400 CFU/ml) | *Y. enterocolitica* (5000 CFU/ml) |
|---|---|---|---|---|---|
| Hb Ib | >40 | 1–5 | 10–20 | 1–5 | 1–5 |
| Hb III | >40 | >20 | >20 | >40 | >40 |
| Bb – A | >40 | 0.5–1 | >20 | >40 | 1–5 |
| Bb + A | >40 | 0.5–1 | 2–10 | 20–40 | 5–10 |
| Ck P | >40 | 1–5 | >20 | >40 | 1–5 |
| Ck A | >40 | 1–5 | >20 | 20–40 | 1–5 |
| Ho– | >40 | 5–10 | >20 | 10–20 | 10–20 |
| Ho+ | 5–10 | 0.5–1 | 2–10 | 1–5 | 1–5 |
| Yj+S | 10–20 | 0.1–0.5 | 2–10 | 0.5–1 | 1–5 |
| Yj–S | 5–10 | 0.1–0.5 | 2–10 | 1–5 | 1–5 |
| Cd 1+ | 10–20 | 10–20 | >20 | 10–20 | 20–40 |
| Cd 1– | 20–40 | 0.5–1 | >20 | 20–40 | 5–10 |
| Cd 2+ | 0.5–1.5 | 0.1–0.5 | 10–20 | 1–5 | 10–20 |
| Cd 2– | 10–20 | 1–5 | 10–20 | 1–5 | >40 |
| Cd 3+ | 0.5–1.5 | 0.1–0.5 | 10–20 | 1–5 | 10–20 |
| Cd 3– | 5–10 | 1–5 | 10–20 | 1–5 | 20–40 |
| CP–1 | 0.2–1 | 1–2 | 2–10 | 0.2–1 | 0.2–1 |

Minimal Inhibitory Concentrations

Specific antibacterial activities of all currently known apidaecin-type peptides were also determined in liquid culture against seven selected bacterial strains (table 4). *E. coli* (wild type and resistant strains) and *S. typhimurium* were chosen as common laboratory strains, Morganella and Yersinia strains for their contrasting apidaecin-analog-antibiograms, and the Acinetobacter strain as a representative of moderately sensitive non-enterobacteriaceae. MIC's were first tested using bacterial cultures with inoculi of about $10^7$ colony forming units (CFU) per ml; no significant killing activities (all MIC's >40 μg/ml) were observed against the Morganella and Yersinia strains, and only peptides Cd2+, Cd3+ and Ho+ had measurable activities against *E. coli* 11775apid$^R$. For those bacterial strains, tests were repeated using an inoculum of $1–5\times10^3$ CFU/ml. This time, MIC's of several peptides were in the low- to sub-microgram/ml range. Thus, an inoculum effect (for definition, see Ref. 45) exists for apidaecin-type antibacterial peptides against certain strains, but not against all, as for example peptides Cd3+ and Ho+ inhibit viability of *E. coli* ATCC11775 equally well with inoculum sizes differing by as much as four orders of magnitude (table 4). No inoculum effect was observed for cecropin P1 with any of the bacterial strains used in this study.

MIC's of cecropin P1 against *E.coli* and Morganella strains were 0.2–1 μg/ml; this is in contrast to the absence of any measurable growth inhibition properties against the same strains on agar plates (table 4). Less dramatic discrepancies between low inhibitory activities on plates and higher ones in liquid culture were also observed for a few apidaecin-type peptides against some strains. While the reason for these discrepancies may be unclear at present, each observation of a strong inhibition zone has invariably been confirmed by low MIC values in culture.

From the numbers presented in table 4, it follows that apidaecin-type peptides have antibacterial activities in the nanomolar to low micromolar range ($5\times10^{-8}$ to $2.5\times10^{-6}$M) against many Enterobacteriaceae; it has been shown previously that specific activities against plant-associated microbes are even better ($10^{-8}$M) (1,24). However, as was already clear from the plate tests, different peptides seem to be selectively better at growth inhibition, or killing, of different bacteria (e.g. Hb Ib against *E. coli* ATCC11775, Ho+ against the Acinetobacter strain and Cd2+ against *E. coli* 11775apid$^R$ mutant strain).

Rescue Polypeptides

One polypeptide isolated from hornets (PAB-FT) (Table 5) has antibacterial activity despite a Proline to Threonine substitution in a highly-conserved region. Experiments were designed to determine whether the Proline-rich N-terminal region of PAB-FT is responsible for "rescuing" activity. Various artificial constructs were made (Table 5). Synthetic polypeptides having the Pro to Thr substitution but lacking the N-terminal proline-rich region (Ho-GT and Ho-FT) lack detectable antibacterial activity, but polypeptides with the N-terminal proline-rich region have antibacterial activity, as determined by their minimal inhibition zone. It was further found that antibacterial activity is rescued by a partial PAB-FT N-terminal region (Table 6).

TABLE V

| Apidaecin related "rescue" peptides: | | |
|---|---|---|
| Peptide (alternative name) | Sequence | [M + H*] |
| Ho+ (=HoGP) | G K P R P Q Q V P P R P P H P R L | 1958.33 (SEQ ID NO: 32) |
| PAB-GP | S R P S P Q V P I R P S Q P R P Q P G K P R P Q Q V P P R P P H P R L | 3964.65 (SEQ ID NO: 33) |
| HoFP (=HoG1F) | F K P R P Q Q V P P R P P H P R L | 2048.45 (SEQ ID NO: 34) |
| PAB-FP | S R P S P Q V P I R P S Q P R P Q P F K P R P Q Q V P P R P P H P R L | 4054.77 (SEQ ID NO: 35) |
| HoGT (=HoP12T) | G K P R P Q Q V P P R T P H P R L | 1962.32 (SEQ ID NO: 36) |
| PAB-GT | S R P S P Q V P I R P S Q P R P Q P G K P R P Q Q V P P R T P H P R L | 3968.63 (SEQ ID NO: 37) |
| HoFT (=HoG1F/P12T) | F K P R P Q Q V P P R T P H P R L | 2052.45 (SEQ ID NO: 38) |
| PAB-FT1-35 | S R P S P Q V P I R P S Q P R P Q P F K P R P Q Q V P P R T P H P R L | 4058.76 (SEQ ID NO: 39) |
| PAB-FT6-35 | Q V P I R P S Q P R P Q P F K P R P Q Q V P P R T P H P R L | 3534.18 (SEQ ID NO: 40) |
| PAB-FT12-35 | S Q P R P Q P F K P R P Q Q V P P R T P H P R L | 2843.33 (SEQ ID NO: 41) |

Of these peptides, only Ho+ and PAB-FT are naturally occurring in hornets; all others are artificial constructs.
Residues that differ from the Ho+ sequences are underlined (except the N-terminal extensions).
Masses are listed as average molecular mass [M] plus [+] 1 proton [$H^+$]

TABLE VI

| Antibacterial activities of apidaecin-type "rescue" peptides | | | | | | | | | | |
|---|---|---|---|---|---|---|---|---|---|---|
| | PEPTIDES | | | | | | | | | |
| BACTERIAL STRAINS | Ho+ | PAB-GP | HoFP | PAB-FP | HoGT | PAB-GT | HoFT | PAB-FT 1-35 | PAB-FT 6-35 | PAB-FT 12-35 |
| *E. coli* ATCC11775 | 15 | 10 | 13 | 10 | – | 8 | – | 10 | 13 | 10 |
| *E. coli* D22 | 14 | 14 | 16 | 14 | – | 13 | – | 14 | 14 | 10 |
| *Salmonella typhimurium* | 14 | 6 | 12 | 7 | – | 6 | – | 7 | 8 | – |
| *Salmonella typhi* | 20 | 13 | 13 | 13 | – | 12 | – | 14 | 14 | 5 |
| *Agrobacterium tumefaciens* | 12 | 8 | 11 | 7 | – | 5 | – | 5 | ND | ND |
| *Erwinia amylovora* | 12 | 5 | 11 | 5 | – | 6 | – | 5 | ND | ND |
| *Pseudomonas syringae* | 13 | 6 | 12 | + | ND | 5 | – | – | ND | ND |
| *Enterobacter cloacae* | 15 | 13 | 14 | 11 | ND | 9 | ND | 11 | 12 | 11 |
| *Klebsiella pneumoniae* | 15 | 9 | 14 | 8 | – | 8 | – | 9 | 11 | 6 |
| *Shigella dysenteriae* | 18 | 11 | 18 | 12 | – | 10 | – | 12 | 12 | 11 |
| *Acinetobacter calcoaceticus* | 5 | 9 | – | 8 | – | 8 | – | 7 | 10 | – |

Inhibition zones: in mm diameter
Peptides: 50 nanomoles per well (3 mm diameter)
ND: Not determined

DISCUSSION

Apidaecin is a small peptide antibiotic (18 L-amino acids, unmodified), isolated from honeybees. It is lethal for many gram negative bacteria in nanomolar doses (1,24) and has a unique 'non-lyric' mechanism that involves stereo-selectivity (Casteels and Tempst, submitted); gram positives are nearly unaffected. Assessment of therapeutic prospects mandates the elucidation of mode-of-action and understanding of the functional role played by each component amino acid. It was decided to look at nature (i.e. evolution) to understand structure / function of this bioactive peptide. Here isolation and structural characterization of 13 novel, naturally occuring apidaecin-type peptides and functional analysis (antibacterial spectra) of 17 members of this class of antibiotics are reported.

The search for novel apidaecin-type peptides was greatly facilitated by the use of immuno-detection (using anti-apidaecin polyclonal antiserum) and mass spectrometric analysis (scanning for molecules in the expected molecular weight range) of liquid chromatographic fractions of induced insect lymph. This not only eliminated the need for tedious antibacterial assays but, most importantly, required consumption of only low nanogram (ELISA) to femtogram (MALDI-TOF MS) quantities of peptide. Typically, the amounts needed for antibacterial assays are on the average one to two orders of magnitude more (1,24). As micro-isolation (29,46), chemical sequencing (33,34) and combined chemical/MS sequencing (31) of small peptides (<25–30 amino acids) are now possible at low picomole levels, less than 50 nanogram of apidaecin-type peptides were required for elucidation of their structures. Thus, studies as described in this report can be undertaken with only a few and/or very small insects as source material. Since the present effort was the first of its kind, antibacterial assays were carried out as a back-up to make sure 'apidaecin-like' peptides that didn't cross-react with the antiserum and, additionally, were unusually big or small would not be overlooked. While, in this way, several novel "other" peptides were discovered, no additional "apidaecin-type" ones were found. Thus, the approach taken here may be more widely applicable.

Sequence alignment of all currently known apidaecin-type peptides allowed delineation of strictly conserved 'core' sequences (FIG. 1). Because the strong reliance of insects on these peptides for survival, and considering the time-scale of divergence within the Hymenoptera order (27), evolutionary pressure on the conserved sequences must have been extraordinary. Hence, it is speculated that these 'core' sequences are essential for general antibacterial capacity. Consistent with this view was the observation that the only apidaecin-type peptide with a substitution in the 'core' sequence (Pro(9) to Ser in Hb III; FIG. 1) is a very poor antibiotic (little to none activity and very narrow spectrum; see tables 2 and 4). This peptide had been chemically synthesized, based on an isoform sequence observed in the open reading frames of some apidaecin cDNA clones. As speculated before (35), this peptide may actually not exist in nature as it is linked in the precursor to an unlikely processing sequence and because it has never been detected in insect lymph (24).

Given that, hitherto, apidaecins (from honeybees) lacked appreciable sequence similarities with other known polypeptides (in NBRF, PIR and SwissProt databases) and because of the presently established high degree of structural conservancy, it is clear that apidaecin-type peptides remain a very distinct group (17 members) of antibacterial molecules. However, when introducing a few gaps for optimal alignment (in FIG. 2), a partial but unmistakable sequence match could be delineated between hornet apidaecin (Ho+) and drosocin from Drosophila (2). The Drosophila peptide however, is glycosilated whereas hornet apidaecin is not. Other Arg-Pro-rich antibacterial peptides have been described, namely insect abaecin (42) and mammalian Bac 5 and 7 (47), and PR-39 (44). None of those can be aligned too easily with apidaecins and they are distinctively lacking in histidine, a conserved residue among apidaecin-type peptides and also present in drosocin (FIGS. 1, 2).

Analysis of biological activities indicated striking differences in antibacterial spectra between several apidaecin-type peptides (tables 2, 3). Structural elements underlying these differences must be located within small stretches of variable amino acid sequence as all apidaecin-type peptides show a high degree of conservation. Thus, functional variability among apidaecin-type peptides could be mapped to just a few amino acids. While this has also been observed for cecropin and magainin antibacterial activities, albeit investigated by comparing artificially designed synthetic analogs (48–50), in those instances, differences were exclusively of a quantitative nature (i.e. higher/lower MIC's against the same strains and as a result, wider/narrower spectra). In contrast, subtle amino acid substitutions in apidaecin-type peptides shift the antibacterial spectrum to a sometimes mutually exclusive pattern. For instance, replacing both Arg and Gln (at positions 4 and 10 in the sequence) with lysines (K/K at 4/10) results in a dramatic decrease of apidaecin activity against Salmonella and completely abolishes activity against Yersinia under the test conditions used; yet, these very changes create a peptide that is highly lethal for *Campylobacter jejuni* and *Legionella pneumophila*, whereas the R/Q-variant was totally ineffective (table 3A). More examples of specificity-determining motifs can be found in table 3. As these motifs are fully contained within the spacer-sequences that separate conserved domains, it seems justified to advance the hypothesis that apidaecin-type peptides consist of 'constant' regions, conferring general antibacterial capacity (i.e. any modifications to these would abolish all function), and 'variable' regions, determining specificity (i.e. antibacterial spectra). Functional variability of these peptides is further highlighted by the remarkable finding that apidaecin-analog-antibiograms of certain bacteria (see table 2) are nearly 'mirror-image' of one another (e.g. Yersinia and Campylobacter), a phenomenon unique among all peptide antibiotics described so far.

The explicit finding that apidaecins antibacterial spectra can be manipulated has inherent practical consequences, i.e. creating peptides with a wider or a targeted narrower spectra. Wider antibacterial spectra can be most easily obtained by administration of several peptides (e.g. HbIb plus Ho+ plus Cd3+) simultaneously. As an alternative, multipotent single molecules may conceivably be constructed by combinatorial shuffling and/or point-substitutions of 'variable' regions, with the restriction however, that some specific killing activities are mutually exclusive. Similarly, designer narrow-spectrum peptides could be derived in this way. Thus, the 'constant/variable region' model will guide the future apidaecin-analog synthesis and testing program. While the significance of broad-spectrum antibacterial chemotherapeutics is generally appreciated, developing a narrow-spectrum drug is less conventional. However, from the data presented here, the synthesis in the not too distant future of an antibacterial drug specific for *Campylobacter jejuni* is envisioned. This microorganism is a food-borne (raw milk) enteric pathogen, causing an estimated 2 million infections in the U.S. each year, and speculated to be a more frequent source of diarrhea in humans than Salmonella and Shigella (51). A specific antibiotic might be useful to treat such infections without affecting the patient's enteric flora (mostly Enterobacterioceae). Along the same lines, an apidaecin-type peptide that would be rationally modified to target plant pathogens exclusively (a goal that doesn't seem overly complicated to attain) could be engineered into transgenic crops, for antimicrobial protection, without affecting man or animal that eat them.

Drug resistance is a major problem in antibacterial chemotherapy (20). Apidaecin could therefore only be considered for clinical applications after suitable 'back-up' peptides have been identified or developed. By virtue of complementarity, four different types of inducible peptides confer broad-spectrum antibacterial defense to honeybees (1). Among those, apidaecins provide protection against the majority of gram negative infections. Evolutionary, potential problems with apidaecin-resistance may have been countered by the synthesis of a second Arg-Pro-rich peptide, abaecin, that is otherwise different in sequence and substantially less active than apidaecin. It has previously been shown that the inhibitory effects of abaecin on an apidaecin-resistant *E. coli* strain (mutant 11775apid$^R$) are unattenuated as compared to the wild-type strain (42). Effective as abaecin may be for coping with sporadic resistance in honeybees, it is probably too low in specific activity to substitute for the highly potent apidaecin in cases like nosocomial infections.

Results of the current study prove that small sequence changes to apidaecin itself also allow to overcome emerging antibacterial resistance (see tables 2 and 4). Furthermore, a Gly-Lys-Pro sequence at the amino-terminus critically determines activity of peptide Ho+ against apidaecin-resistant strain 11775apid$^R$, as removal of this triplet abolishes lethal capacity against the mutant but not against the parental strain. These observations, together with the fact that mutant and parent strain are equally susceptible (resistant) to 'lyric' peptides (e.g. cecropin P1, magainin B) (25), refute the notion that the emerging apidaecin-resistance was the result of a simple barrier mutation (i.e. physically excluding passage of antibiotic through the cell envelope). Barrier-mutations, affecting outer membrane structure and/or protein content, have typically been implicated in bacterial resistance to lyric peptides. For example, resistance of Salmonella to polymixin B action has been correlated with an altered pmrA gene (52).

The present findings are therefore in keeping with earlier observations that apidaecin-type peptides exert antibacterial activities through a non-lyric mechanism, involving stereoselective interactions (25). The total picture emerging is consistent with the view that specific molecular recognition, between peptide and bacterial "receptor/docking" molecule(s), underlies lethal function of apidaecin-type peptides. Strain-specific variation (sequence differences) and novel alterations (mutations) of these chiral 'target-molecules' might constitute the molecular basis for, respectively, drug-specificity and -resistance. This speculation is founded in the known *E. coli* quinolone-resistance mechanisms (53), whereby various selected alterations in DNA gyrase result in differential 'resistance' phenotypes (e.g. the same point mutation causing sensitivity to nalidixic acid to go down but that to the structurally related norfloxacin to go up). Conceivably then, combinations of several apidaecin-type peptides, with diverse 'variable' regions, may prevent resistance from easily emerging.

Finally, while 'target-molecules' could reside on the bacterial surface, the notion that, after apidaecin binding, a lethal 'signal' would be transmitted to upset vital structures or functions inside the cell, is hard to comprehend. In addition, with a molecular weigth of over 2,000 dalton, apidaecin is probably too big to utilize the outer membrane porins for passive influx. Then how would the peptide get into the cells? Colicins (antibacterial proteins of bacterial origin) are known to do so by utilizing host membrane receptors (e.g. for vitamin B12 or nucleotides) for inward translocation (54); once inside, they interact with a second target molecule, causing cessation of vital cell function or death. It is a provocative thought that apidaecins might do the same.

BIBLIOGRAPHY

1. Casteels, P., Ampe, C., Jacobs, F., and Tempst, P. (1993) *J. Biol. Chem.* 268, 7044–7054.
2. Bulet, P., Dimarcq, J. L., Hetru, C., Lagueux, M., Charlet, M., Hegy, G., Van Dorsselaer, A., and Hoffmann J. A. (1993) *J. Biol. Chem.* 268, 14893–14897.
3. Lehrer, R. I., Lichtenstein, A. K., and Ganz, T. (1993) *Ann. Rev. Immunol.* 11, 105–128.
4. Christensen, B., Fink, J., Merrifield, R. B., and Mauzerall, D. (1988) *Proc. Natl Acad. Sci. USA* 85, 5072–5076.
5. Cruciani, R. A., Barker, J. L., Zasloff, M., Chen, H. C., and Colamonici, O. (1991) *Proc. Natl. Acad. Sci. USA* 88, 3792–3796.
6. Viljanen, P., Koski, P., and Vaara, M. (1988) *Infect. Immun.* 56, 2324–2329.
7. Skerlavaj, B., Romeo, D. , and Gennaro, R. (1990) *Infect. Immun.* 58, 3724–3730.
8. Okada, M., and Natori, S. (1985) *Biochem. J.* 229, 453–458.
9. Matsuyama, K., and Natori, S. (1990) *J. Biochem.* 108, 128–132.
10. Keppi, E., Pugsley, A. P., Lambert, J., Wicker, C., Dimarcq, J.-L., Hoffmann, J. A., and Hoffmann, D. (1989) *Arch. Insect. Biochem. physiol.* 10, 229–239.
11. Ohta, M., Ito, H., Masuda, K., Tanaka, S., Arakawa, Y., Wacharotayankun, R., and Kato, N. (1992) *Antimicrob. Agents Chemother.* 36, 1460–1465.
12. Lee, S., Mihara, H., Aoyagi, H., Kato, T., Izumiya, N., and Yamasaki, N. (1986) *Biochim. Biophys. Acta* 862, 211–219.
13. Westerhoff, H. V., Juretic, D., Hendler, R. W., and Zasloff, M. (1989) *Proc. Natl. Acad. Sci. USA* 86, 6597–6601.
14. De Lorenzo, V., and Pugsley, A. P. (1985) *Antimicrob. Agents Cheroother.* 27, 666–669.
15. Wade, D., Boman, A., Wahlin, B., Drain, C. M., Andreu, D., Boman, H. G., and Merrifield, R. B. (1990) *Proc. Natl. Acad. Sci. USA* 87, 4761–4765.
16. Besalle, R., Kapitkovsky, A., Gorea, A., Shalit, I., and Fridkin M. (1990) *FEBS Lett.* 274, 151–155.
17. Andreu, D., Merrifield, R. B., Steiner, H., and Boman, H. G. (1987) *Biochemistry* 24, 1683–1688.
18. Steiner, H., Andreu, D., and Merrifield, R. B. (1988) *Biochim. Biophys. Acta* 939, 260–266.
19. Klastersky, J. , Zinner, S. H., Calandra, T., Gaya, H., Glauser, M. P., Meunier, F., Rossi, M., Schimpff, S. C., Tattersall, M., and Viscoli, C. (1988) *Eur. J. Cancer. Clin. Oncol.* 24, S35–S45.
20. Neu, H. C. (1992) *Science* 257, 1064–1073.
21. Bryan, L. E. (1989) *J. Antimicrob. Chemother.* 23, 817–823.
22. McGowan, J. E., Barnes, M. W., and Finland, M. (1975) *J. Infect. Dis.* 132, 316–335.
23. Meyer, R. D. (1983) *Rev. Infect. Dis.* 5, 258–2787.
24. Casteels, P., Ampe, C., Jacobs, F., Vaeck, M., and Tempst, P. (1989) *EMBO J.* 8, 2387–2391.
25. Casteels, P., and Tempst, P. (*Biochem. Biophys. Res. Commun.*, in press ).
26. Houghten, R. A., Pinilla, C. Blondelie, S. E., Appel, J. R., Dooley, C. T., and Cuervo, J. H. (1991) *Nature* 354, 84–86.
27. Borror, D. J., De Long, D. M., and Triplehorn, C. A. (1981) *An Introduction to the Study of Insects*, 5th Ed, W. B. Saunders, Philadelphia, PA.
28. Holden, C. (1989) *Science* 246, 754–756.
29. Tempst, P., Link, A. J., Riviere, L. R., Fleming, M., and Elicone, C. (1990) *Electrophoresis* 11, 537–553.
30. Harlow, E., and Lane, D. (1988) *Antibodies: a Laboratory Manual*, Cold Spring Harbor Laboratory, Cold Spring Harbor, N.Y.

31. Geromanos, S., Casteels, P., Elicone, C., Powell, M., and Tempst, P. (1994) in *Techniques in Protein Chemistry V* (Crabb, J.W., ed), Academic Press, San Diego, Calif., In Press.
32. Hewick, R. M., Hunkapiller, M. W., Hood, L. E., and Dreyer, W. J. (1981) *J. Biol. Chem.* 256, 7990–7997.
33. Tempst, P., and Riviere, L. (1989) *Anal. Biochem.* 183, 290–300.
34. Erdjument-Bromage, H., Geromanos, G., Chodera, A., and Tempst, P. (1993) in *Techniques in Protein Chemistry IV* (Hogue-Angeletti, R., ed) pp. 419–426, Academic Press, San Diego, Calif.
35. Casteels-Josson, K., Capaci, T., Casteels, P., and Tempst, P. (1993) EMBO J. 12, 1569–1578.
36. Nolan, C., and Margoliash, E. (1968) *Ann. Rev. Biochem.* 37, 727–781.
37. Neu, H. C., Chin, N. X., and Novelli, A. (1988) *Antimicrob. Agents Chemother.* 32, 1666–1675.
38. Jones, R. N., Barry, A. L., and Thornsberry, C. (1989) *Antimicrob. Agents Chemother.* 33, 944–950.
39. Joklik, W. K., Willerr, H. P., Amos, D. B., and Wilfert, C. M. (1992) *Zinsser Microbiology,* 20th Ed, Appleton & Lange, Norwalk, Conn.
40. Lenette, E. H., Balows, A., Hausler, W. J., and Shadomy, H. J., Eds. (1985) *Manual of Clinical Microbiology,* 4th Ed, American Society for Microbiology, Washington, D.C.
41. Miller, S. I., Pulkkinen, W. S., Selsted, M. E., and Mekalanos, J. J. (1990) Infect. Immun. 58, 3706–3710.
42. Casteels, P., Ampe, C., Riviere, L., Van Damme, J., Elicone, E., Fleming, M., Jacobs, F., and Tempst, P. (1990) *Eur. J. Blochem.* 187, 381–386.
43. Casteels, P. (1990) *Ph.D. Thesis*, Ghent State University, Ghent, Belgium.
44. Agerberth, B., Lee, J. Y., Bergman, T., Carlquist, M., Boman, H. G., Mutt, V., and Jornvall, H. (1991) *Eur. J. Blochem.* 202, 849–854.
45. Amsterdam, D. (1991) in *Antibiotics in Laboratory Medicine,* 3rd Ed (Lorian, V., ed) , Williams and Wilkins, Baltimore, Md.
46. Henzel, W. J., Bourell, J. H., and Stults, J. T. (1990) *Anal. Biochem.* 187, 228–233.
47. Frank, R. W., Gennaro, R., Schneider, K., Przybylsky, M., and Romeo, D. (1990) *J. Biol. Chem.* 265, 18871–18874.
48. Andreu, D. , Merrifield, R. B., Steiner, H., and Boman, H. G. (1985) *Biochemistry* 24, 1683–1688.
49. Li, Z-Q., Merrifield, R. B., Boman, A., and Boman, H. G. (1988) *FEBS Lett.* 231, 299–302.
50. Chen, H.-C., Brown, J. H., Morell, J.L., and Huang, C. M. (1988) *FEBS Lett.* 236, 462–466.
51. Morris, G. K., and Patton, C. M. (1985) in *Manual of Clinical Microbiology,* 4th Ed (Lenette, E. H., Balows, A., Hausler, W. J., and Shadomy, H. J., eds), American Society for Microbiology, Washington, D.C.
52. Vaara, M., Vaara, T., Jensen, M., Helander, I., Nurminen, M., Rietschel, E. T. and Makela, P. H. (1981) *FEBS Lett.* 129, 145–149.
53. Hooper, D. C., and Wolfson, J. C. (1985) in *Antibiotics in Laboratory Medicine,* 3rd Ed (Loria, V., ed), Willies and Wilkins, Baltimore, Md.
54. Konisky, J. (1982) *Ann. Rev. Microbiol.* 36, 125–144.

What is claimed is:

1. A purified polypeptide having antibacterial activity, comprising:

a first sequence Pro-Arg-Pro-Pro-His-Pro-Arg-(Ile/Leu) (SEQ ID NO: 1);

optionally, a second sequence immediately adjacent to the N-terminal amino acid residue of the first sequence, wherein the second sequence is selected from the group consisting of:
Pro;
Ala;
Gln;
Ile-Gln; and
Ile-Lys;

a third sequence immediately adjacent to the second sequence, or immediately adjacent to the N-terminal amino acid residue of the first sequence when the polypeptide does not contain a second sequence, wherein the third sequence has the following formula: X2-Pro-X3-X4-X5-Pro (SEQ ID NO: 2), wherein
X2 is Arg or Lys;
X3 is Thr, Gln or Arg;
X4 is Tyr, Gln or Pro; and
X5 is Val or Ala; and a fourth sequence immediately adjacent to the third sequence, wherein the fourth sequence is selected from the group consisting of:
Asn;
(Gly/Phe)-Lys-Pro;
Ser-Asn-Lys-Pro (SEQ ID NO: 42); and
Gly-Lys-Pro-(Asn/Ser) (SEQ ID NO: 43);

wherein the fourth sequence is truncated by zero to four amino acid residues at its N-terminus; and wherein the number of amino acid residues in the polypeptide is the sum of the number of second sequence residues, the number of fourth sequence residues, and fourteen.

2. The polypeptide of claim 1, wherein the third sequence is selected from the group consisting of:

Arg-Pro-Thr-Tyr-Val-Pro (SEQ ID NO: 3);

Arg-Pro-Gln-Gln-Val-Pro (SEQ ID NO: 4);

Arg-Pro-Arg-Pro-Ala-Pro (SEQ ID NO: 5); and

Lys-Pro-Arg-Pro-Ala-Pro (SEQ ID NO: 6).

3. The polypeptide of claim 1, selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Arg—Pro—Gln—Gln—Val—Pro—Pro—Arg—Pro—Pro—His—Pro—Arg—Leu (SEQ ID NO: 10);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

4. A method for inhibiting growth of a bacterium comprising administering to the bacterium a growth inhibiting effective concentration of the polypeptide of claim 1.

5. The method of claim 4 for inhibiting growth of a bacterium selected from the group consisting of

*Escherichia coli, Enterobacter cloacae, Erwinia amylovora, Klebsiella pneumoniae, Salmonella typhimurium, Shigella dysenteriae*, and *Pseudomonas syringae*.

comprising administering to the bacterium a growth inhibiting effective concentration of a polypeptide of claim 3.

6. The method of claim 5 for inhibiting growth of an apidaecin resistant strain of *Escherichia coli* comprising administering a growth inhibiting effective concentration of a polypeptide selected from the group consisting of:

| |
|---|
| Gly—Lys—Pro—Arg—Pro—Gln—Gln—Val—Pro—Pro—Arg—Pro—Pro—His—Pro—Arg—Leu (SEQ ID NO: 9); |
| Ser—Asn—Lys—Pro—Arg—Pro—Gln—Gln—Val—Pro—Pro—Arg—Pro—Pro—His—Pro—Arg—Leu (SEQ ID NO: 11); |
| Asn—Lys—Pro—Arg—Pro—Gln—Gln—Val—Pro—Pro—Arg—Pro—Pro—His—Pro—Arg—Leu (SEQ ID NO: 12); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and |
| Ser—Lys—Pro—Arg—Pro—Ala—Pro—Ile—Lys—Pro—Arg—Pro—Pro—His—Pro—Arg—Leu (SEQ ID NO: 18). |

7. The method of claim 4 for inhibiting growth of *Morganella morganii* comprising administering a growth inhibiting effective concentration of a polypeptide selected from the group consisting of:

| |
|---|
| Gly—Lys—Pro—Arg—Pro—Gln—Gln—Val—Pro—Pro—Arg—Pro—Pro—His—Pro—Arg—Leu (SEQ ID NO: 9); |
| Arg—Pro—Gln—Gln—Val—Pro—Pro—Arg—Pro—Pro—His—Pro—Arg—Leu (SEQ ID NO: 10); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and |
| Ser—Lys—Pro—Arg—Pro—Ala—Pro—Ile—Lys—Pro—Arg—Pro—Pro—His—Pro—Arg—Leu (SEQ ID NO: 18). |

8. The method of claim 4 for inhibiting growth of *Salmonella typhi* comprising administering a growth inhibiting effective concentration of a polypeptide selected from the group consisting of:

| |
|---|
| Asn—Arg—Pro—Thr—Tyr—Val—Pro—Pro—Pro—Arg—Pro—Pro—His—Pro—Arg—Leu (SEQ ID NO: 7); |
| Asn—Arg—Pro—Thr—Tyr—Val—Pro—Ala—Pro—Arg—Pro—Pro—His—Pro—Arg—Leu (SEQ ID NO: 8); |
| Gly—Lys—Pro—Arg—Pro—Gln—Gln—Val—Pro—Pro—Arg—Pro—Pro—His—Pro—Arg—Leu (SEQ ID NO: 9); |
| Arg—Pro—Gln—Gln—Val—Pro—Pro—Arg—Pro—Pro—His—Pro—Arg—Leu (SEQ ID NO: 10); |
| Ser—Asn—Lys—Pro—Arg—Pro—Gln—Gln—Val—Pro—Pro—Arg—Pro—Pro—His—Pro—Arg—Leu (SEQ ID NO: 11); |
| Asn—Lys—Pro—Arg—Pro—Gln—Gln—Val—Pro—Pro—Arg—Pro—Pro—His—Pro—Arg—Leu (SEQ ID NO: 12); |
| Gly—Lys—Pro—Asn—Arg—Pro—Arg—Pro—Ala—Pro—Ile—Gln—Pro—Arg—Pro—Pro—His—Pro—Arg—Leu (SEQ ID NO: 13); |
| Asn—Arg—Pro—Arg—Pro—Ala—Pro—Ile—Gln—Pro—Arg—Pro—Pro—His—Pro—Arg—Leu (SEQ ID NO: 14); |
| Gly—Lys—Pro—Asn—Lys—Pro—Arg—Pro—Ala—Pro—Ile—Lys—Pro—Arg—Pro—Pro—His—Pro—Arg—Leu (SEQ ID NO: 15); |
| Asn—Lys—Pro—Arg—Pro—Ala—Pro—Ile—Lys—Pro—Arg—Pro—Pro—His—Pro—Arg—Leu (SEQ ID NO: 16); and |
| Gly—Lys—Pro—Ser—Lys—Pro—Arg—Pro—Ala—Pro—Ile—Lys—Pro—Arg—Pro—Pro—His—Pro—Arg—Leu (SEQ ID NO: 17). |

9. The method of claim 4 for inhibiting growth of *Yersinia*

*enterocolitica* comprising administering a growth inhibiting effective concentration of a polypeptide selected from the group consisting of:

---

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Arg—Pro—Gln—Gln—Val—Pro—Pro—Arg—Pro—Pro—His—Pro—Arg—Leu (SEQ ID NO: 10);
Asn—Lys—Pro—Arg—Pro—Gln—Gln—Val—Pro—Pro—Arg—Pro—Pro—His—Pro—Arg—Leu (SEQ ID NO: 12); and
Asn—Arg—Pro—Arg—Pro—Ala—Pro—Ile—Gln—Pro—Arg—Pro—Pro—His—Pro—Arg—Leu (SEQ ID NO: 14).

---

10. The method of claim 4 for inhibiting growth of *Campylobacter jejuni* comprising administering growth inhibiting effective concentration of polypeptide selected from the group consisting of:

---

Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

---

11. The method of claim 4 for inhibiting growth of *Acinetobacter calcoaceticus* comprising administering a growth inhibiting effective concentration of a polypeptide selected from the group consisting of:

---

Gly—Lys—Pro—Arg—Pro—Gln—Gln—Val—Pro—Pro—Arg—Pro—Pro—His—Pro—Arg—Leu (SEQ ID NO: 9);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

---

12. The method of claim 4 for inhibiting growth of *Agrobacterium tumefaciens* comprising administering a growth inhibiting effective concentration of a polypeptide selected from the group consisting of:

---

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—

-continued

Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

13. The method of claim 4 for inhibiting growth of *Francisella tularensis* or *Haemophilus influenzae* comprising administering a growth inhibiting effective concentration of a polypeptide selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Ser—Asn—Lys—Pro—Arg—Pro—Gln—Gln—Val—Pro—Pro—Arg—Pro—Pro—His—Pro—Arg—Leu (SEQ ID NO: 11);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

14. The method of claim 4 for inhibiting growth of *Legionella pneumophila* comprising administering a growth inhibiting effective concentration of a polypeptide selected from the group consisting of:

Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

15. The method of claim 4 for inhibiting growth of *Rhizobium meliloti* comprising administering a growth inhibiting effective concentration of a polypeptide selected from the group consisting of:

Asn—Arg—Pro—Thr—Tyr—Val—Pro—Pro—Pro—Arg—Pro—Pro—His—Pro—Arg—Leu (SEQ ID NO: 7);
Asn—Arg—Pro—Thr—Tyr—Val—Pro—Ala—Pro—Arg—Pro—Pro—His—Pro—Arg—Leu (SEQ ID NO: 8);
Gly—Lys—Pro—Arg—Pro—Gln—Gln—Val—Pro—Pro—Arg—Pro—Pro—His—Pro—Arg—Leu (SEQ ID NO: 9);
Arg—Pro—Gln—Gln—Val—Pro—Pro—Arg—Pro—Pro—His—Pro—Arg—Leu (SEQ ID NO: 10);
Asn—Lys—Pro—Arg—Pro—Gln—Gln—Val—Pro—Pro—Arg—Pro—Pro—His—Pro—Arg—Leu (SEQ ID NO: 12);
Gly—Lys—Pro—Asn—Arg—Pro—Arg—Pro—Ala—Pro—Ile—Gln—Pro—Arg—Pro—Pro—His—Pro—Arg—Leu (SEQ ID NO: 13);
Asn—Arg—Pro—Arg—Pro—Ala—Pro—Ile—Gln—Pro—Arg—Pro—Pro—His—Pro—Arg—Leu (SEQ ID NO: 14);
Gly—Lys—Pro—Asn—Lys—Pro—Arg—Pro—Ala—Pro—Ile—Lys—Pro—Arg—Pro—Pro—His—Pro—Arg—Leu (SEQ ID NO: 15);
Asn—Lys—Pro—Arg—Pro—Ala—Pro—Ile—Lys—Pro—Arg—Pro—Pro—His—Pro—Arg—Leu (SEQ ID NO: 16);
Gly—Lys—Pro—Ser—Lys—Pro—Arg—Pro—Ala—Pro—Ile—Lys—Pro—Arg—Pro—Pro—His—Pro—Arg—Leu (SEQ ID NO: 17); and
Ser—Lys—Pro—Arg—Pro—Ala—Pro—Ile—Lys—Pro—Arg—Pro—Pro—His—Pro—Arg—Leu (SEQ ID NO: 18).

* * * * *